United States Patent [19]
Ponte et al.

[11] Patent Number: 5,220,013
[45] Date of Patent: Jun. 15, 1993

[54] DNA SEQUENCE USEFUL FOR THE DETECTION OF ALZHEIMER'S DISEASE

[75] Inventors: Phyllis A. Ponte, Mountain View; Barbara Cordell, Palo Alto, both of Calif.

[73] Assignee: Scios Nova Inc., Mountain View, Calif.

[21] Appl. No.: 444,118

[22] Filed: Nov. 30, 1989

Related U.S. Application Data

[63] Continuation-in-part of Ser. No. 87,002, Aug. 18, 1987, abandoned, which is a continuation-in-part of Ser. No. 8,810, Jan. 30, 1987, abandoned, which is a continuation-in-part of Ser. No. 948,376, Dec. 31, 1986, abandoned, which is a continuation-in-part of Ser. No. 932,193, Nov. 17, 1986, abandoned.

[51] Int. Cl.[5] .............................................. C08B 1/04
[52] U.S. Cl. ...................................... 536/23.5; 435/6; 436/811; 530/324; 935/11; 536/24.31
[58] Field of Search ...................... 435/172.3, 320.1, 6; 935/11, 77, 78; 436/811; 536/27; 530/324

[56] References Cited

U.S. PATENT DOCUMENTS 4,595,674 6/1986 Tschesche et al.
4,666,829 5/1987 Glenner et al. .......................... 435/6
4,912,206 3/1990 Goldgaber et al.

OTHER PUBLICATIONS

Van Nostrand et al., *Journal of Biological Chemistry*, (1987) 262(18):8508–8514.
Robakis et al., *Proc Natl Acad Sci USA* 84:4190–4194 (Jun. 1987).
Kang et al., *Nature* 325:733–736 (Feb. 19, 1987).
Goldgaber et al., *Science* 235:877–880 (Feb. 1987).
Neve et al., *Biological Abstracts* 83(6):1987.
Tanzi et al., *Science* 235:880–884 (Feb. 1987).
Masters et al., *Chemical Abstracts* 104(15) (Apr. 1986), pp. 506–507.
Masters et al., *EMBO J* 4(1):2757–2763 (1985).
Uzan et al., *Biochem Biophys Res Comm* 119:273–281 (Feb. 1984).
Masters et al., *Proc Natl Acad Sci USA* 82:4245–4249 (Jun. 1985).
Glenner and Wong, *Biochem Biophys Res Comm* 120(3):885–890 (May 1984).
Glenner et al., *Biochem Biophys Res Comm* 122:1131–1135 (Aug. 1984).
Glenner et al., "Amyloidosis", published by Plenum Press, Jun. 1986, pp. 693–701.
Roher et al., *Proc Natl Acad Sci USA* 82:2662–2666 (Apr. 1986).
Wong et al., *Proc Natl Acad Sci USA* 82:8729–8732 (Dec. 1985).
Ohtsuka et al., *Biol Chem* 269:2605–2608 (Mar. 1985).
Takahashi et al., *Proc Natl Acad Sci USA* 82:1931–1935 (Apr. 1985).
Robakis et al., *Proc Natl Acad Sci USA* 83:6377–6381 (1986).
Allsop et al., *Neuroscience Letters* 68:252–256 (1986).
Price et al., *Drug Development Res* 5:59–68 (1985).
Delabar et al., *Science* 235:1390–1392 (1987).

(List continued on next page.)

*Primary Examiner*—Amelia Burgess Yarbrough
*Attorney, Agent, or Firm*—Morrison & Foerster

[57] ABSTRACT

DNA sequences encoding the beta-amyloid core protein, and beta-amyloid-related proteins associated with Alzheimer's disease are disclosed. These sequences are used in producing or constructing recombinant beta-amyloid core protein, beta-amyloid-related proteins and recombinant or synthetic immunogenic peptides. These sequences are also used to identify genomic mutations and/or restriction site alterations which are associated with a predisposition to Alzheimer's disease, for purposes of genetic screening. Antibodies generated against the recombinant proteins or immunogenic peptides derived therefrom can be used for cerebral fluid or serum protein diagnosis of Alzheimer's disease.

5 Claims, 25 Drawing Sheets

```
                                                ATG CTG CCC
                                                Met Leu Pro

GGT TTG GCA CTG CTC CTG CTG GCC GCC TGG ACG GCT CGG GCG CTG GAG GTA CCC
Gly Leu Ala Leu Leu Leu Leu Ala Ala Trp Thr Ala Arg Ala Leu Glu Val Pro
                              10                                    20

ACT GAT GGT AAT GCT GGC CTG CTG GCT GAA CCC CAG ATT GCC ATG TTC TGT GGC
Thr Asp Gly Asn Ala Gly Leu Leu Ala Glu Pro Gln Ile Ala Met Phe Cys Gly
                                    30

AGA CTG AAC ATG CAC ATG AAT GTC CAG AAT GGG AAG TGG GAT TCA GAT CCA TCA
Arg Leu Asn Met His Met Asn Val Gln Asn Gly Lys Trp Asp Ser Asp Pro Ser
40                      50
GGG ACC AAA ACC TGC ATT GAT ACC AAG GAA GGC ATC CTG CAG TAT TGC CAA GAA
Gly Thr Lys Thr Cys Ile Asp Thr Lys Glu Gly Ile Leu Gln Tyr Cys Gln Glu
          60                                    70

GTC TAC CCT GAA CTG CAG ATC ACC AAT GTG GTA GAA GCC AAC CAA CCA GTG ACC
Val Tyr Pro Glu Leu Gln Ile Thr Asn Val Val Glu Ala Asn Gln Pro Val Thr
                    80                                    90

ATC CAG AAC TGG TGC AAG CGG GGC CGC AAG CAG TGC AAG ACC CAT CCC CAC TTT
Ile Gln Asn Trp Cys Lys Arg Gly Arg Lys Gln Cys Lys Thr His Pro His Phe
                          100                                    110

GTG ATT CCC TAC CGC TGC TTA GTT GGT GAG TTT GTA AGT GAT GCC CTT CTC GTT
Val Ile Pro Tyr Arg Cys Leu Val Gly Glu Phe Val Ser Asp Ala Leu Leu Val
                                120

CCT GAC AAG TGC AAA TTC TTA CAC CAG GAG AGG ATG GAT GTT TGC GAA ACT CAT
Pro Asp Lys Cys Lys Phe Leu His Gln Glu Arg Met Asp Val Cys Glu Thr His
130                                      140
```

OTHER PUBLICATIONS

Barnes, *Science* 235:846–847 (1987).
Anderton, *Nature* 325:658–659 (1987).
Selkoe et al., *Science* 235:873–876 (1987).
Allsop et al., *Brain Res* 259:348–352 (1983).
Westermark and Cornwell, *Amyloidosis*, pp. 659–668 (1984).
Allsop et al., *Amyloidosis*, pp. 723–732 (1984).
St. George-Hyslop et al., *Science* 235:885–890 (1987).
Ponte et al., *Nature*, 331(6156):525–527 (1988).
Tanzi et al., *Nature* 331:528–530 (1988).
Kitaguchi et al., *Nature* 331:530–532 (1988).
Shivers et al., *EMBO J* 7(5):1365–1370 (1988).
Dyrks et al., *EMBO J* 7(4):949–957 (1988).
Marks et al., *J Biol Chem* 261(16):7115–7118 (1986).
Tan and Kaiser, *Biochem* 16(8):1531–1541 (1977).
Gebhard et al., *Protease Inhibitors*, Barrett and Salvesen (eds.), 1986, Elsevier Science Publishers BV, pp. 375–388.
Fritz and Wunderer, *Drug Res* 33(1):479–494 (1983).
Carrell, *Nature* (1988) 331:478–479.

FIG. 1A

```
        ATG CTG CCC
        MET Leu Pro

GGT TTG GCA CTG CTC CTG CTG GCC GCC TGG ACG GCT CGG GCG CTG GAG GTA CCC
Gly Leu Ala Leu Leu Leu Leu Ala Ala Trp Thr Ala Arg Ala Leu Glu Val Pro
                    10                                            20

ACT GAT GGT AAT GCT GGC CTG CTG CTG GCT GAA CCC CAG ATT GCC ATG TTC TGT GGC
Thr Asp Gly Asn Ala Gly Leu Leu Leu Ala Glu Pro Gln Ile Ala MET Phe Cys Gly
                                        30

AGA CTG AAC ATG CAC ATG AAT GTC CAG AAT GGG AAG TGG GAT TCA GAT CCA TCA
Arg Leu Asn MET His MET Asn Val Gln Asn Gly Lys Trp Asp Ser Asp Pro Ser
 40                                          50

GGG ACC AAA ACC TGC ATT GAT ACC AAG GAA GGC GGG ATC CTG CAG TAT TGC CAA GAA
Gly Thr Lys Thr Cys Ile Asp Thr Lys Glu Gly Gly Ile Leu Gln Tyr Cys Gln Glu
         60                                            70

GTC TAC CCT GAA CTG CAG ATC ACC AAT GTG GTA GAA GCC AAC CAA CCA CAT CCC CAC TTT
Val Tyr Pro Glu Leu Gln Ile Thr Asn Val Val Glu Ala Asn Gln Pro His Pro His Phe
                     80                                     90                   110

ATC CAG AAC TGG AAG TGC CGC GGG GGC CGC AAG CAG TGC AAG ACC GAT GCC CTT CTC GTT
Ile Gln Asn Trp Lys Cys Arg Gly Gly Arg Lys Gln Cys Lys Thr Asp Ala Leu Leu Val
                         100

GTG ATT CCC TAC CGC TGC TTA GTT GGT GAG TTT GTA AGT GAT GTT TGC GAA ACT CAT
Val Ile Pro Tyr Arg Cys Leu Val Gly Glu Phe Val Ser Asp Val Cys Glu Thr His
                                         120

CCT GAC AAG TGC AAA TTC TTA CAC CAG GAG AGG ATG GAT GTT TGC GAA ACT CAT
Pro Asp Lys Cys Lys Phe Leu His Gln Glu Arg MET Asp
130                                            140
```

FIG. 1B

```
CTT CAC TGG CAC ACC GTC GCC AAA GAG ACA TGC AGT GAG AAG AGT ACC AAC TTG
Leu His Trp His Thr Val Ala Lys Glu Thr Cys Ser Glu Lys Ser Thr Asn Leu
            150                                 160

CAT GAC TAC GGC ATG TTG CTG CCC TGC GGA ATT GAC AAG TTC CGA GGG GTA GAG
His Asp Tyr Gly MET Leu Leu Pro Cys Gly Ile Asp Lys Phe Arg Gly Val Glu
            170                                 180

TTT GTG TGT TGC CCA CTG GCT GAA GAA AGT GAC AAT GTG GAT TCT GCT GAT GCG
Phe Val Cys Cys Pro Leu Ala Glu Glu Ser Asp Asn Val Asp Ser Ala Asp Ala
            190                                 200

GAG GAG GAT GAC TCG GAT GTC TGG TGG GGC GGA GCA GAC ACA GAC TAT GCA GAT
Glu Glu Asp Asp Ser Asp Val Trp Trp Gly Gly Ala Asp Thr Asp Tyr Ala Asp
            210

GGG AGT GAA GAC AAA GTA GTA GAA GCA GAG GAA GTG GCT GAG GTG
Gly Ser Glu Asp Lys Val Val Glu Ala Glu Glu Val Ala Glu Val
            220                                 230

GAA GAA GAA GAA GCC GAT GAT GAC GAT GAG GAT GGT GAT GAG GTA GAG
Glu Glu Glu Glu Ala Asp Asp Asp Asp Glu Asp Gly Asp Glu Val Glu
            240                                 250

GAA GAG GCT GAG GAA CCC TAC GAA GAA GCC ACA GAG ACC ACC AGC ATT GCC
Glu Glu Ala Glu Glu Pro Tyr Glu Glu Ala Thr Glu Thr Thr Ser Ile Ala
            260                                 270

ACC ACC ACC ACC ACA GAG TCT GTG GAA GAG GTG GTT CGA GAG GTG TGC
Thr Thr Thr Thr Thr Glu Ser Val Glu Glu Val Val Arg Glu Val Cys
            280                                 290
```

FIG. 1C

```
TCT GAA CAA GCC GAG ACG GGG CCG TGC CGA GCA ATG ATC TCC CGC TGG TAC TTT
Ser Glu Gln Ala Glu Thr Gly Pro Cys Arg Ala MET Ile Ser Arg Trp Tyr Phe
                              300

GAT GTG ACT GAA GGG AAG TGT GCC CCA TTC TTT TAC GGC GGA TGT GGC GGC AAC
Asp Val Thr Glu Gly Lys Cys Ala Pro Phe Phe Tyr Gly Gly Cys Gly Gly Asn
310                                     320

CGG AAC AAC TTT GAC ACA GAA GAG TAC TGC ATG GCC GTG TGT GGC AGC GCC ATT
Arg Asn Asn Phe Asp Thr Glu Glu Tyr Cys MET Ala Val Cys Gly Ser Ala Ile
            330                                     340

CCT ACA GCA GCC AGT ACC CCT GAT GCC GTT GAC GCC AAG TAT CTC GAG ACA CCT
Pro Thr Ala Ala Ser Thr Pro Asp Ala Val Asp Ala Lys Tyr Leu Glu Thr Pro
                350                                     360

GGG GAT GAG AAT GAA CAT GCC CAT TTC CAG AAA GCC AAA GAG AGG CTT GAG GCC
Gly Asp Glu Asn Glu His Ala His Phe Gln Lys Ala Lys Glu Arg Leu Glu Ala
                        370                                     380

AAG CAC CGA GAG ATG TCC CAG GTC ATG AGA GAA TGG GAA GAG GCA GAA CGT
Lys His Arg Glu MET Ser Gln Val MET Arg Glu Trp Glu Ala Glu Arg
                            390

CAA GCA AAG AAC TTG CCT AAA GCT GAT AAG AAG CTG AAA GCA GTT ATC CAG CAT TTC CAG
Gln Ala Lys Asn Leu Pro Lys Ala Asp Lys Lys Lys Ala Val Ile Gln His Phe Gln
400                                     410

GAG AAA GTG GAA TCT TTG GAA CAG GAA CAG GCC AAC GAG AGA CAG CAG CTG GTG
Glu Lys Val Glu Ser Leu Glu Gln Glu Gln Ala Asn Glu Arg Gln Gln Leu Val
420                                     430

GAG ACA CAC ATG GCC AGA GTG GAA GCC ATG CTC AAT GAC CGC CGC CGC CTG GCC
Glu Thr His MET Ala Arg Val Glu Ala MET Leu Asn Asp Arg Arg Arg Leu Ala
                440                                     450
```

FIG. 1D

```
CTG GAG AAC TAC ATC ACC GCT CTG CAG GCT GTT CCT CGG CCT CGT CAC GTG
Leu Glu Asn Tyr Ile Thr Ala Leu Gln Ala Val Pro Arg Pro Arg His Val
460                                                              470

TTC AAT ATG CTA AAG AAG TAT GTC CGC GCA GAA CAG AAG GAC AGA CAG ACC
Phe Asn MET Leu Lys Lys Tyr Val Arg Ala Glu Gln Lys Asp Arg Gln Thr
                    480

CTA AAG CAT TTC GAG CAT GTG CGC ATG GTG GAT CCC AAG AAA GCC GCT CAG ATC
Leu Lys His Phe Glu His Val Arg MET Val Asp Pro Lys Lys Ala Ala Gln Ile
490                              500

CGG TCC CAG GTT ATG ACA CAC CTC CGT GTG ATT TAT GAG CGC ATG AAT CAG TCT
Arg Ser Gln Val MET Thr His Leu Arg Val Ile Tyr Glu Arg MET Asn Gln Ser
510                              520

CTC TCC CTG CTC TAC AAC GTG CCT GCA GTG GCC GAG GAG ATT CAG GAT GAA GTT
Leu Ser Leu Leu Tyr Asn Val Pro Ala Val Ala Glu Glu Ile Gln Asp Glu Val
530                              540

GAT GAG CTG CTT CAG AAA GAG CAA AAC TAT TCA GAT GAC GTC TTG GCC AAC ATG
Asp Glu Leu Leu Gln Lys Glu Gln Asn Tyr Ser Asp Asp Val Leu Ala Asn MET
            550                                                  560

ATT AGT GAA CCA AGG ATC AGT TAC GGA AAC GAT GCT CTC ATG CCA TCT TTG ACC
Ile Ser Glu Pro Arg Ile Ser Tyr Gly Asn Asp Ala Leu MET Pro Ser Leu Thr
                        570

GAA ACG AAA ACC ACC GTG GAG CTC CTT CCC GTG AAT GGA GAG TTC AGC CTG GAC
Glu Thr Lys Thr Thr Val Glu Leu Leu Pro Val Asn Gly Glu Phe Ser Leu Asp
580                              590

GAT CTC CAG CCG TGG CAT TCT TTT GGG GCT GAC TCT GTG CCA GCC AAC ACA GAA
Asp Leu Gln Pro Trp His Ser Phe Gly Ala Asp Ser Val Pro Ala Asn Thr Glu
        600                                              610
```

```
AAC GAA GTT GAG CCT GTT GAT GCC CGC CCT GCC GAC CGA GGA CTG ACC ACT
Asn Glu Val Glu Pro Val Asp Ala Arg Pro Ala Asp Arg Gly Leu Thr Thr
            620                         630

CGA CCA GGT TCT GGG TTG ACA AAT ATC AAG ACG GAG GAG ATC TCT GAA GTG AAG
Arg Pro Gly Ser Gly Leu Thr Asn Ile Lys Thr Glu Glu Ile Ser Glu Val Lys
            640                                                     650

ATG GAT GCA GAA TTC CGA CAT GAC TCA GGA TAT GAA GTT CAT CAT CAA AAA TTG
MET Asp Ala Glu Phe Arg His Asp Ser Gly Tyr Glu Val His His Gln Lys Leu
                        660

GTG TTC TTT GCA GAA GAT GTG GGT TCA AAC AAA GGT GCA ATC ATT GGA CTC ATG
Val Phe Phe Ala Glu Asp Val Gly Ser Asn Lys Gly Ala Ile Ile Gly Leu MET
670                                         680

GTG GGC GGT GTT GTC ATA GCG ACA GTG ATC ACC TTG GTG ATG CTG AAG
Val Gly Gly Val Val Ile Ala Thr Val Ile Thr Leu Val MET Leu Lys
    690                                 700

AAG AAA CAG TAC ACA TCC ATT CAT CAT GGT GTG GAG GTT GAC GCC GCT GTC
Lys Lys Gln Tyr Thr Ser Ile His His Gly Val Glu Val Asp Ala Ala Val
            710                                             720

ACC CCA GAG GAG CGC CAC CTG TCC AAG ATG CAG CAG AAC GGC TAC GAA AAT CCA
Thr Pro Glu Glu Arg His Leu Ser Lys MET Gln Gln Asn Gly Tyr Glu Asn Pro
                    730                                             740

ACC TAC AAG TTC TTT GAG CAG ATG CAG AAC TAG
Thr Tyr Lys Phe Phe Glu Gln MET Gln Asn
                    750
```

```
                                                                    27                                               54
TTT TTG TTC AAA ATA GGT AGT AAT TGA · AGT TTT AAA TAT AGG GTA TCA TTT TTC
Phe Leu Phe Lys Ile Gly Ser Asn  ·    Ser Phe Lys Tyr Arg Val Ser Phe Phe 81                                              108
TTT AAG AGT CAT TTA TCA ATT TTC TTC TAA · CTT CAG GCC TAG AAA GAA GTT TTG
Phe Lys Ser His Leu Ser Ile Phe Phe  ·    Leu Gln Ala  ·  Lys Glu Val Leu 135                                              162
GGT AGG CTT TGT CTT ACA GTG TTA TTT ATG AGT AAA ACT AAT TGG TTG TCC
Gly Arg Leu Cys Leu Thr Val Leu Phe MET Ser Lys Thr Asn Trp Leu Ser

Hind II
                                                                                      ↓
                                                                   189                                              216
TGC ATA CTT TAA TTA TGA TGT AAT ACA│GGT TCT GGG TTG ACA AAT ATC AAG ACG
Cys Ile Leu  ·  Leu  ·  Cys Asn Thr│Gly Ser Gly Leu Thr Asn Ile Lys Thr EcoRI
                                            ↓
                                                                   243                                              270
GAG ATC TCT GAA GTG AAG ATG GAT GCA│TTC CGA CAT GAC TCA GGA TAT
Glu Ile Ser Glu Val Lys MET Asp Ala│Phe Arg His Asp Ser Gly Tyr
                                    1                       5                                                        10
```

```
                          Rsa I ↓ |297                                              324
GAA GTT CAT CAT CAA AAA TTG GTA  CGT AAA ATA ATT TAC CTC TTT CCA CTA CTG
Glu Val His His Gln Lys Leu Val  Arg Lys Ile Ile Tyr Leu Phe Pro Leu Leu
                    15            18

351                                                                              378
TTT GTC TTG CCA AAT GAC CTA TTA ACT CTG GTT CAT CCT GTG CTA GAA ATC AAA
Phe Val Leu Pro Asn Asp Leu Leu Thr Leu Val His Pro Val Leu Glu Ile Lys 405                                                                              432
TTA AGG AAA AGA TAA AAA TAC AAT GCT TGC CTA TAG GAT TAC CAT GAA AAC ATG
Leu Arg Lys Arg  .  Lys Tyr Asn Ala Cys Leu  .  Asp Tyr His Glu Asn MET 459                                                                              486
AAG AAA ATA AAT AGG CTA GGC TGA GCG CAG TGG CTC AAG CCT GTA ATC CCA GCA
Lys Lys Ile Asn Arg Leu Gly  .  Ala Gln Trp Leu Lys Pro Val Ile Pro Ala
```

```
         10         20         30         40         50         60         70
GAATTCCCCT GGGAGCCAAA GGAATTGGGA ATGTGTAGCC CAAGTAAGAC AAGAACCAGC AGGAACATGC
         80         90        100        110        120        130        140
CTCTCCTTAG GGTCGTGATA CCTGTTCAAG GTTTTAATGT GGAAGGGAGG ATTAGGCTTG CTCTGTGTTG
        150        160        170        180        190        200        210
AATCAGGCTC AAAGGATGGA AGTTACAGGG AAGCTGATTC TGGCTTCATG TAAAAAAGG ACAGTTTGGG
        220        230        240        250        260        270        280
CAGGCAAATC TATCAAAAAA TGGAGGGAAA TTGATACATT CCTCTATGTT CAAACAGGAA CTGACAATCT
        290        300        310        320        330        340        350
GCCCCTGGGT GGGAACACGG TAGAGAAGAT GACTTCAAAA GCCCTTTTCA TCCTAAAATT CTGATGTTTG
        360        370        380        390        400        410        420
ATAATTAAAT GTTATAGCAT GGACACTGAC ATTTACATTT TTTACTTATG TTTTTGGTTT TTAAATGACT
        430        440        450        460        470        480        490
CTGCATTTTG TTTTAAGCTT CAAATTATTA TTTGAATAAT GAAATTCATC AGAACAATTA GTGTTAAGAA
        500        510        520        530        540        550        560
TCATATAGCA ATTTATAGAA AAGGAAGAGT TCGTAGGTTA TAAATTCTGT TAGTTGCTAA GAAGCATTTT
        570        580        590        600        610        620        630
TAAAATTATG TACTATAGCT CTTTATTCAG CAGACGAACC AATTACAATC TGTGTAACTA GAACACTTGA
```

```
      640          650          660          670          680          690          700
CTAAAATTAT ATAATTTTTA CAACGCTTCA CTGCATAGAT ACATGAACAT AATTTATTTG TAATTGGAAC 710          720          730          740          750          760          770
AAAGCCCCAA AGTAGCAGTT TTGTTCTACC AGGTAATTAA TGCTCATTTT TAAAGCCTTT TATTATTATT 780          790          800          810          820          830          840
TCTGAAGTAA TGAGTGCACA TGGAAAAAGA CACATAATAG GCTAAACAAT AAGCCCGTAA GCCAAGCCAA 850          860          870          880          890          900          910
CATATTCCAG GAACAAATCC TTGCCAACCT CTCAACCAGG ATTTAACTTC TGCTTTTCCC CCATTTCAA 920          930          940          950          960          970          980
AAATTATAGC ATGTATTTAA AGGCAGCAGA AGCCTTACTT TCAGGTTTCC CTTACCCTTT CATTTCTTTT 990          1000         1010         1020         1030         1040         1050
TGTTCAAAAT AGGTAGTAAT TGAAGTTTTA AATATAGGGT ATCATTTTTC TTTAAGAGTC ATTTATCAAT 1060         1070         1080         1090         1100         1110         1120
TTTCTTCTAA CTTCAGGCCT AGAAAGAAGT TTTGGGTAGG CTTTGTCTTA CAGTGTTATT ATTTATGAGT 1130         1140         1150         1160         1170         1180         1190
AAAACTAATT GGTTGTCCTG CATACTTTAA TTATGATGTA ATACAGGTTC TGGGTTGACA AATATCAAGA 1200         1210                            1228
CGGAGGAGAT CTCTGAAGTG AAG ATG GAT GCA GAA TTC
                         MET Asp Ala Glu Phe
                          1   2   3   4
```

```
GAA TTC CGA CAT GAC TCA GGA TAT GAA GTT CAT CAT CAA AAA TTG GTG TTC TTT
Glu Phe Arg His Asp Ser Gly Tyr Glu Val His His Gln Lys Leu Val Phe Phe
 3                           10                              20

GCA GAT GTG GGT TCA AAC AAA GGT GCA ATC ATT GGA CTC ATG GTG GGC GGT
Ala Glu Asp Val Gly Ser Asn Lys Gly Ala Ile Ile Gly Leu MET Val Gly Gly
                     30

GTT GTC ATA GCG ACA GTG ATC GTC ACC TTG GTG ATG CTG AAG AAA AAA CAG
Val Val Ile Ala Thr Val Ile Val Thr Leu Val MET Leu Lys Lys Lys Gln
 40                                        50

TAC ACA TCC ATT CAT CAT GGT GTG GAG GTT GAC GCC GCT GTC ACC CCA GAG
Tyr Thr Ser Ile His His Gly Val Val Glu Val Asp Ala Ala Val Thr Pro Glu
                 60                                        70

GAG CGC CAC CTG TCC AAG ATG CAG CAG AAC GGC TAC GAA AAT CCA ACC TAC AAG
Glu Arg His Leu Ser Lys MET Gln Gln Asn Gly Tyr Glu Asn Pro Thr Tyr Lys
                     80                                        90

TTC TTT GAG CAG ATG CAG AAC TAG ACCCCCGCCA CAGCAGCCTC TGAAGTTGGA CAGCAAAACC
Phe Phe Glu Gln MET Gln Asn
                 99
       344        354        364        374        384        394        404
ATTGCTTCAC TACCCATCGG TGTCCATTTA TAGAATAAATG TGGGAAGAAA CAAACCCGTT TTATGATTTA 414        424        434        444        454        464        474
CTCATTATCG CCTTTTGACA GCTGTGCTGT AACACAAGTA AATGCCTGAA CTTGAATTAA TCCACACATC 484        494        504        514        524        534        544
AGTAATGTAT TCTATCTCTC TTTACATTTT GGTCTCTATA CTACATTATT AATGGGTTTT GTGTACTGTA
```

FIG. 4B

```
     554        564        574        584        594        604        614
AAGAATTTAG CTGTATCAAA CTAGTGCATG AATAGATTCT CTCCTGATTA TTTATCACAT AGCCCCTTAG 624        634        644        654        664        674        684
CCAGTTGTAT ATTATTCTTG TGGTTTGTGA CCCAATTAAG TCCTACTTTA CATATGCTTT AAGAATCGAT 694        704        714        724        734        744        754
GGGGGATGCT TCATGTGAAC GTGGGAGTTC AGCTGCTTCT CTTGCCTAAG TATTCCTTTC CTGATCACTA 764        774        784        794        804        814        824
TGCATTTTAA AGTTAAACAT TTTTAAGTAT TTCAGATGCT TTAGAGAGAT TTTTTTTCCA TGACTGCATT 834        844        854        864        874        884        894
TTACTGTACA GATTGCTGCT TCTGCTATAT TTGTGATATA GGAATTAAGA GGATACACAC GTTTGTTTCT 904        914        924        934        944        954        964
TCGTGCCTGT TTTATGTGCA CACATTAGGC ATTGAGACTT CAAGCTTTTC TTTTTTTGTC CACGTATCTT 974        984        994       1004       1014       1024       1034
TGGGTCTTTG ATAAAGAAAA GAATCCCTGT TCATTGTAAG CACTTTTACG GGGCGGGTGG GGAGGGGTGC 1044       1054
TCTGCTGGTC TTCAATTACC AAGAATTC
```

```
ATG GAT GCA GAA TTC CGA CAT GAC TCA GGA TAT GAA GTT CAT CAT
Met Asp Ala Glu Phe Arg His Asp Ser Gly Tyr Glu Val His His
 0                                        10

CAA AAA TTG GTG TTC TTT GCA GAA GAT GTG GGT TCA AAC AAA
Gln Lys Leu Val Phe Phe Ala Glu Asp Val Gly Ser Asn Lys
                20

GGT GCA ATC ATT GGA CTC ATG GTG GGC GGT GTT GTC ATA GCG
Gly Ala Ile Ile Gly Leu Met Val Gly Gly Val Val Ile Ala
    30                                    40

ACA GTG ATC GTC ATC ACC TTG GTG ATG CTG AAC AAG AAA CAG
Thr Val Ile Val Ile Thr Leu Val Met Leu Lys Lys Lys Gln
                    50

TAC ACA TCC ATT CAT CAT GGT GTG GTG GAG GTT GAC GCC GCT
Tyr Thr Ser Ile His His Gly Val Val Glu Val Asp Ala Ala
            60                                        70

GTC ACC CCA GAG GAG CGC CAC CTG TCC AAG ATG CAG CAG AAC
Val Thr Pro Glu Glu Arg His Leu Ser Lys Met Gln Gln Asn
                                    80

GGC TAC GAA AAT CCA ACC TAC AAG TTC TTT GAG CAG ATG CAG
Gly Tyr Glu Asn Pro Thr Tyr Lys Phe Phe Glu Gln Met Gln
                    90

AAC
Asn
```

```
GAA TTC GGA CAT GAT TCA GGA TTT GAA GTC CGC CAT CAA AAA CTG GTG TTC TTT
Glu Phe Gly His Asp Ser Gly Phe Glu Val Arg His Gln Lys Leu Val Phe Phe
 3                          10                 27                     54
                                                                      20

GCT GAA GAT GTG GGT TCG AAC AAA GGC GCC ATC ATC GGA CTC ATG GTG GGC GGC
Ala Glu Asp Val Gly Ser Asn Lys Gly Ala Ile Ile Gly Leu MET Val Gly Gly
                         81                  30                      108

GTT GTC ATA GCA ACC GTG
Val Val Ile Ala Thr Val
             135
 40
```

FIG. 7A  Nucleotide Comparison

```
W3  GAA TTC CGA CAT GAC TCA GGA TAT GAA GTT CAT CAT CAA AAA TTG GTG TTC TTT   54
         X                    X         X   X  XX             X
W9  GAA TTC GGA CAT GAT TCA GGA TTT GAA GTC CGC CAT CAA AAA CTG GTG TTC TTT   54
                                                27

W3  GCA GAA GAT GTG GGT TCA AAC AAA GGT GCA ATC ATT GGA CTC ATG GTG GGC       108
      X                     X          X       X                       
W9  GCT GAA GAT GTG GGT TCG AAC AAA GGC GCC ATC ATC GGA CTC ATG GTG GGC       108
                                81

W3  GTT GTC ATA GCG ACA GTG                                                    135
                 X   X                                                          
W9  GTT GTC ATA GCA ACC GTG                                                    135
```

FIG. 7B   Amino Acid Comparison

```
W3  Glu Phe Arg His Asp Ser Gly Tyr Glu Val His His Gln Lys Leu Val Phe Phe
             X                      X
W9  Glu Phe Gly His Asp Ser Gly Phe Glu Val Arg His Gln Lys Leu Val Phe Phe

W3  Ala Glu Asp Val Gly Ser Asn Lys Gly Ala Ile Ile Gly Leu MET Val Gly Gly
W9  Ala Glu Asp Val Gly Ser Asn Lys Gly Ala Ile Ile Gly Leu MET Val Gly Gly

W3  Val Val Ile Ala Thr Val
W9  Val Val Ile Ala Thr Val
```

FIG. 8A Junction
FIG. 8B Insert
FIG. 8C Actin

FIG. 9A

```
          1
    CACCTGTCCAAGATGCAGCAGAACGGCTACGAACGGCTACGAAATCCAACCTACAAGTTCTTTGAGCAGATGCAGAACTA
    CGCGGGTGGACAGGTTCTACGTCGTCTTGCCGATGCTTTTAGGTTGGATGTTCAAGAAACTCTGCTACGTCTTGATTCGA
    HaeII       2              3                4            5            6    HindII
              289
```

```
    GluPheAsnGlyGluValCysSerGluGlnAlaGluThrGlyProCysArgAlaMetIleSerArgTrpTyrPheAspVal
    AATTCAACGGCGAGGTGCTCTGAACAAGCTGAGACTGGCCCGTGCCGTGCAATGATCTCCCGCTGGTACTTTGATGTG
    GTTGCGCGCTCCACACGAGACTTGTTCGACTCTGACTCTGACCGGGCACGGTTACTAGAGGGGCGACCATGAAACTACAC
    EcoRI
```

```
    ThrGluGlyLeuLysCysCysAlaProPhePheTyrGlyGlyCysGlyGlyAsnArgAsnAsnPheAspThrGluGluTyrCysMet
    ACTGAAGGTAAGTGCGCTCCATTCTTTTACGGTGGTTGCGGCGGCAACCGTAACAACTTTGACACTGAAGAGTACTGCATG
    TGACTTCCATTCACGCGAGGTAAGAAAATGCCGCCAACGCCGCGTTGGCATTGTTGAAACTGTGACTTCTCATGACGTAC
```

```
    AlaValCysGlySerAlaIleTER
    GCAGTGTGCGGCAGCGCTATTTAAGGATCCA
    CGTCACACGCCGTCGCGATAAATTCCTAGGTTCGA
                    BamHIHindIII
                345
```

FIG. 9D

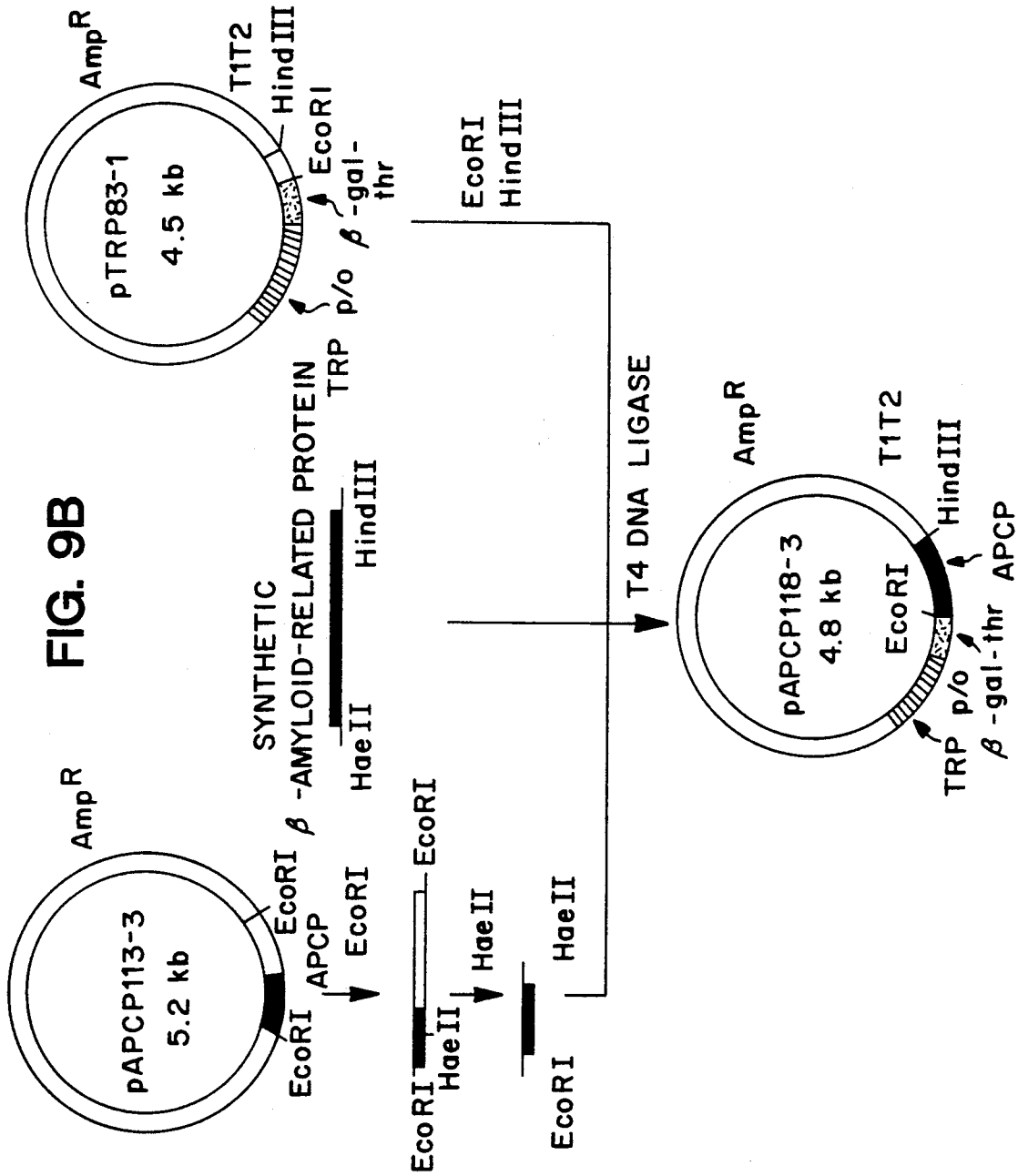

FIG. 9C

NH₂-Met-Thr-Ile-Thr-Leu-Thr-Thr-Thr-Thr-Thr-Thr- (beta-gal-thr leader)

655
Glu-Phe-Arg-His-Asp-Ser-Gly-Tyr-Glu-Val-His-His-Gln-Lys-Leu-Val-Phe-Phe-Ala-

Glu-Asp-Val-Gly-Ser-Asn-Lys-Gly-Ala-Ile-Ile-Gly-Leu-Met-Val-Gly-Gly-Val-Val-

Ile-Ala-Thr-Val-Ile-Val-Ile-Thr-Leu-Val-Met-Leu-Lys-Lys-Lys-Gln-Tyr-Thr-Ser-

Ile-His-His-Gly-Val-Val-Glu-Val-Asp-Ala-Ala-Val-Thr-Pro-Glu-Glu-Arg-His-Leu-

Ser-Lys-Met-Gln-Gln-Asn-Gly-Tyr-Glu-Asn-Pro-Thr-Tyr-Lys-Phe-Phe-Glu-Gln-Met-

751
Gln-Asn-COOH (B-amyloid-related polypeptide)

FIG. 13A

TIHUBI : Inter-alpha-trypsin inhibitor (BPI type)
50.0% identity in 52 aa overlap

```
INSERT      1"  AVLPQEEGSGGGQLVTEVTKKEDSCQLGYSAGPCMGMTSRYFYNGTSMACETFQYGGCM
INSERT      1'                     EVCSEQAETGPCRAMISRWYFDVTEGKCAPFFYGGCGGNRN
                                   :.. :::::.: :  :::..:::. : :::. ::
TIHUBI     61"  GNGNNFVTEKECLQTCRTVAACNLPVIRGPCRAFIQLWAFDAVKGKCVLFPYGGCQGNGN

42' NFDTEEYCMAVCGSAI
                .: .: ::: ::
           121" KFYSEKECREYCGVPGDEDEEELL
```

TIBOBI : Inter-alpha-trypsin inhibitor (BPI type)
48.1% identity in 54 aa overlap

```
INSERT      1"                                                            EV
INSERT      1"  KADSCQLDYSQGPCLGLFKRYFYNGTSMACETFLYGGCMGNLNNFLSQKECLQTCRTVEA
                                                                          :.:
             3' CSEQAETGPCRAMISRWYFDVTEGKCAPFFYGGCGGNRNNFDTEEYCMAVCGSAI
                :.. ::::::.: :  :::..: :::. : :::. ::  ::: ::: ::
TIBOBI     61"  CNLPIVQGPCRAFIQLWAFDAVKGKCVRFSYGGCKGNGNKFYSQKECKEYCGIPGEADER

TIBO : Basic protease inhibitor precursor - Bovine
47.4% identity in 57 aa overlap

```
INSERT    1'                 EVCSEQAETGPCRAMISRWYFDVTEGKCAPFFYGGCGGNRNNFD
                              . : ... :::.: :......:  :.:  ::::  ..:::.
TIBO      1"  PSLFNRDPPIPAAQRPDFCLEPPYTGPCKARIIRYFYNAKAGLCQTFVYGGCRAKRNNFK

45'  TEEYCMAVCGSAI
              ..: :: .:::::
         61"  SAEDCMRTCGGAIGPWGKTGGRAEGEGKG
```

TIBOR : Serum basic protease inhibitor - Bovine
42.9% identity in 56 aa overlap

```
INSERT    1'                EVCSEQAETGPCRAMISRWYFDVTEGKCAPFFYGGCGGNRNNFDTEEYCMAVCGSA
                             . : ... :.......:  :.:  ::::  ..:::.:  ::  .::.:
TIBOR     1"  TERPDFCLEPPYTGPCKAAMIRYFYNAKAGFCETFVYGGCRAKSNNFKSAEDCMRTCGGA

57'  I
```

DNA SEQUENCE USEFUL FOR THE DETECTION OF ALZHEIMER'S DISEASE

CROSS-REFERENCE TO RELATED APPLICATIONS

This application claims priority to U.S. Ser. No. 07/359,911, filed May 12, 1989, which is the U.S. National Stage Application of PCT W088/03951, filed Nov. 12, 1987, which is a continuation-in-part of U.S. Ser. No. 087,002, filed Aug. 18, 1987 (abandoned), which is a continuation-in-part of U.S. Ser. No. 008,810, filed Jan. 30, 1987 (abandoned), which is a continuation-in-part of U.S. Ser. No. 948,376, filed Dec. 31, 1986 (abandoned), which is a continuation-in-part of U.S. Ser. No. 932,193, filed Nov. 17, 1986 (abandoned).

TECHNICAL FIELD

The invention relates to the diagnosis and treatment of Alzheimer's disease. More specifically, it relates to the use of materials related to amyloid protein deposits associated with Alzheimer's disease for diagnosis.

BACKGROUND ART

The demography of Alzheimer's disease is becoming progressively better understood. It is estimated that over 5% of the U.S. population over 65 and over 15% of the U.S. population over 85 are beset with this disease (Cross, A. J., *Eur J Pharmacol* (1982) 82:77-80; Terry, R. D. et al., *Ann Neurol* (1983) 14:497-506). It is believed that the principal cause for confinement of the elderly in long term care facilities is due to this disease, and approximately 65% of those dying in skilled nursing facilities suffer from it.

To confound the problem that therapy is at present a matter of experimentation, diagnosis is also unreliable. There is no straightforward diagnostic test, and diagnosis is made by a series of evaluations based on negative results for alternative explanations for the symptomologies exhibited. Assuming that the presence of the disease can be assessed accurately after death by autopsies of the brain, current results show that present diagnostic methods among living individuals carry an approximately 20% rate of false positives.

It would be extremely helpful in effecting appropriate care for patients and in developing therapies to have a straightforward assay method for diagnosing the presence of Alzheimer's disease. The invention described below provides an approach to this diagnosis.

Certain facts about the biochemical and metabolic phenomena associated with the presence of Alzheimer's disease are known. Two morphological and histopathological changes noted in Alzheimer's disease brains are neurofibrillary tangles (NFT) and amyloid deposits. Intraneuronal neurofibrillary tangles are present in other degenerative diseases as well, but the presence of amyloid deposits both in the interneuronal spaces (neuritic plaques) and in the surrounding microvasculature (vascular plaques) seems to be characteristic of Alzheimer's. Of these, the neuritic plaques seem to be the most characteristic (Price, D. L. et al., *Drug Development Research* (1985) 5:59-68).

The protein which makes up the bulk of these plaques has been partially purified and sequenced. Plaque-rich brains of deceased Alzheimer's patients have been used as a source to extract an approximately 4.2 kd "core" polypeptide, amyloid plaque core protein (APCP), herein referred to as "beta-amyloid core protein." This peptide was designated B-protein by Glenner, G., et al., [*Biochem Biophys Res Commun* (1984) 120:885-890]. The amino acid sequence of the amino-terminus has been determined [Glenner, G., et al., *Biochem Biophys Res Commun* (1984) 122:1131-1135; Masters, C. L., et al., *Proc Natl Acad Sci USA* (1985) 82:4245-4259]. The amino acid sequences reported by the two groups above are identical except that Glenner et al., report a glutamine at position 11 for Alzheimer Disease cerebral vascular amyloid whereas Masters et al., report glutamic acid at position 11. Also, the former authors report that the cerebral vascular amyloid has a unique amino-terminus while the latter authors report that the form found in amyloid plaque cores has a "ragged" amino-terminus—i.e., peptides isolated from this source appear to be missing 3, 7, or 8 amino acids from the amino-terminus. Both groups have shown that the same peptide is found in the amyloid plaque cores and vascular amyloid of adult Downes syndrome-afflicted individuals and report glutamic acid at position 11.

Further studies on the beta-amyloid core protein were also conducted by Roher, A. et al., *Proc Natl Acad Sci USA* (1986) 83:2662-2666 which showed the complete amino acid composition of the protein, and verified that it matched that of no known protein. The compositions those of Allsop, D., et al., *Brain Res* (1983) 259:348-352; nor were they in agreement with those published by Glenner or Masters (supra).

Wong, C. W. et al., *Proc Natl Acad Sci USA* (1985) 82:8729-8732 showed that a synthetic peptide which was homologous to the first ten amino acids of the beta-amyloid core protein described by Masters (supra) was able to raise antibodies in mice and that these antibodies could be used to stain not only amyloid-laden cerebral vessels, but neuritic plaques as well. These results were confirmed by Allsop, D. et al., *Neuroscience Letters* (1986) 68:252-256 using monoclonal antibodies directed against a synthetic peptide corresponding to amino acids 8-17. Thus, in general, the plaque protein found in various locations of the brain of Alzheimer's patients appears to be similar in immunoreactivity. It is highly insoluble, as shown by the inability to achieve solubilization in many commonly used denaturants such as detergents and chaotropic agents (Masters, supra, Allsop, D., et al., (supra)).

It is believed, by analogy to other amyloid proteins, that beta-amyloid core protein may be formed from a precursor in the peripheral circulatory system or lymphatic system. There are six known instances of disease-associated amyloid deposits in which the nature of the precursor protein for the amyloid protein is known: for primary amyloidosis, the source is an immunoglobulin light chain; for secondary amyloidosis, the precursor is amyloid A protein; for familial amyloid polyneuropathy and senile cardiac amyloidosis, prealbumin or a variant thereof; for medullary carcinoma of thyroid, a procalcitonin fragment; and for hereditary cerebral hemorrhage, gamma-trace fragment (See, e.g., Glenner, G. *New England Journal of Medicine* (1980) 302:1283; Sletton, K. et al., *Biochem J* (1981) 195:561; Benditt, et al., *FEBS Lett* (1971) 19:169; Sletton, K., et al., *Eur J Biochem* (1974) 41:117; Sletton, K., et al., *J Exp Med* (1976) 143:993). The foregoing is a partial list and there are at least a number of additional references with regard to procalcitonin fragment as a precursor for the amyloid of the thyroid carcinoma. Alternatively, or additionally, such a precursor for beta-amyloid core protein may be produced in the brain.

It has been described that a protein containing the beta-amyloid core protein sequence within the framework of a larger protein exists (Kang, J et al., *Nature* (1987) 325:733-736). This protein, which is a potential precursor in vivo to the beta-amyloid core protein, was predicted from the sequence of a cDNA clone isolated from a human fetal brain tissue cDNA library and consists of 695 amino acid residues wherein the amino terminus of the beta-amyloid core protein begins at position 597. By analogy to the above described series, it may be that such a precursor or a fragment thereof circulates in the serum at a level differentiable in Alzheimer's victims relative to unafflicted individuals. Alternatively or additionally, such differences may be detected in the cerebral spinal fluid.

An alternative mechanism which could lead to the production of a beta-amyloid core protein in vivo is suggested by the observation that the sequences encoding the first amino acid (Asp) of the beta-amyloid core protein is directly proceeded in the genome by the codon for a methionine, which is the initiating amino acid for protein synthesis. Selection of this methionine by the translational apparatus of a cell as an initiator methionine, followed by its enzymatic removal by an aminopeptidase as frequently occurs in vivo, would give rise to a protein with the amino terminus of the beta-amyloid core protein.

DISCLOSURE OF THE INVENTION

It is one general object of the invention to provide DNA sequence and protein compositions for beta-amyloid-related proteins which can be used for improved screening, diagnosis, characterization, and study of the etiology of Alzheimer's disease.

In particular, the invention provides an isolated native, cloned, recombinant or synthetic DNA sequence useful in the prognosis and diagnosis of Alzheimer's disease in human subjects comprising the DNA sequence of FIG. 1.

In a preferred embodiment of this aspect of the invention is provided a DNA sequence wherein a subfragment of the sequence shown in FIG. 1 corresponds to the 168 basepair insert fragment of the beta-amyloid-related gene product of bacteriophage lambda ACPC1-68i4.

In yet another aspect of the invention, recombinant beta-amyloid-related proteins obtained by the expression of the above-described DNA sequences are provided.

A further aspect of the invention relates to a method of diagnosing a genetic predisposition to Alzheimer's disease in a test subject, comprising identifying, as being associated with predisposition to Alzheimer's disease, one or more alterations in the afore-described DNA, and assaying test subject gene fragments for the presence or absence of such alteration(s).

A further embodiment provides a method of diagnosing Alzheimer's disease in a test subject, comprising preparing a peptide which includes an immunogenic region of the novel protein, eliciting antibodies which are specific against peptide, and using the antibodies to detect the increase or decrease of beta-amyloid-related proteins in a test subject suspected of having Alzheimer's disease.

Yet a further embodiment of the invention relates to a novel protease inhibitor of the sequence:

Glu Val Cys Ser Glu Gln Ala Glu Thr Gly Pro Cys Arg Ala

Met Ile Ser Arg Trp Tyr Phe Asp Val Thr Glu Gly Lys Cys

Ala Pro Phe Phe Tyr Gly Gly Cys Gly Gly Asn Arg Asn Asn

Phe Asp Thr Glu Glu Tyr Cys Met Ala Val Cys Gly Ser Ala

Ile.

These and other objects and features of the invention will become more fully apparent when the following detailed description of the invention is read in conjunction with the accompanying drawings.

BRIEF DESCRIPTION OF THE DRAWINGS

FIG. 1 shows the base sequence of a cDNA clone, designated lambda APCP168i4, which encodes amino acids 1-751 of beta-amyloid-related protein. The 168 bp insert, which distinguishes this clone from the Kang et al. sequence, is underlined.

FIG. 2 shows a DNA sequence of a genomic clone encoding the first 18 amino acids of the beta-amyloid core protein as described by Masters et al. It also encodes, immediately preceding these amino acids, a methionine codon which could potentially be used as an initiating codon.

FIG. 3 shows the base sequence of a cDNA clone, designated lambda SM2W4, whose 3' end encodes the first four amino acids of beta-amyloid core protein. It also encodes, immediately preceding these amino acids, a methionine codon as described above.

FIG. 4 shows the base sequence of a cDNA clone, designated lambda SM2W3, which encodes 97 amino acids; the first 26 of these correspond to the region of the beta-amyloid core protein described by Masters et al., from $Glu_3$ through $Ala_{28}$.

FIG. 5 shows the base sequence and corresponding amino acid sequence of a beta-amyloid-related protein deduced from lambda SM2W4 and lambda SM2W3.

FIG. 6 shows the nucleotide and deduced amino acid sequence of the lambda SMW9 beta-amyloid clone.

FIG. 7 shows a comparison of the sequences of lambda SM2W3 and lambda SM2W9.

FIG. 8 shows the detection of mRNAs for lambda APCP168i4 and the mRNA described by Kang et al. on a Northern blot produced using RNA's isolated from human brain and human cells in culture and hybridized to oligonucleotide probes which are specific for each species.

FIG. 9 shows the construction scheme for a bacterial expression vector for the production of a beta-amyloid-related protein in bacteria.

FIG. 13 shows the relatedness of the peptide encoded by the lambda APCP168i4 168 bp insert to a superfamily of proteins many of whose members exhibit inhibitory activity for basic proteases.

DETAILED DESCRIPTION OF THE INVENTION

A. Definitions

Figure 10:
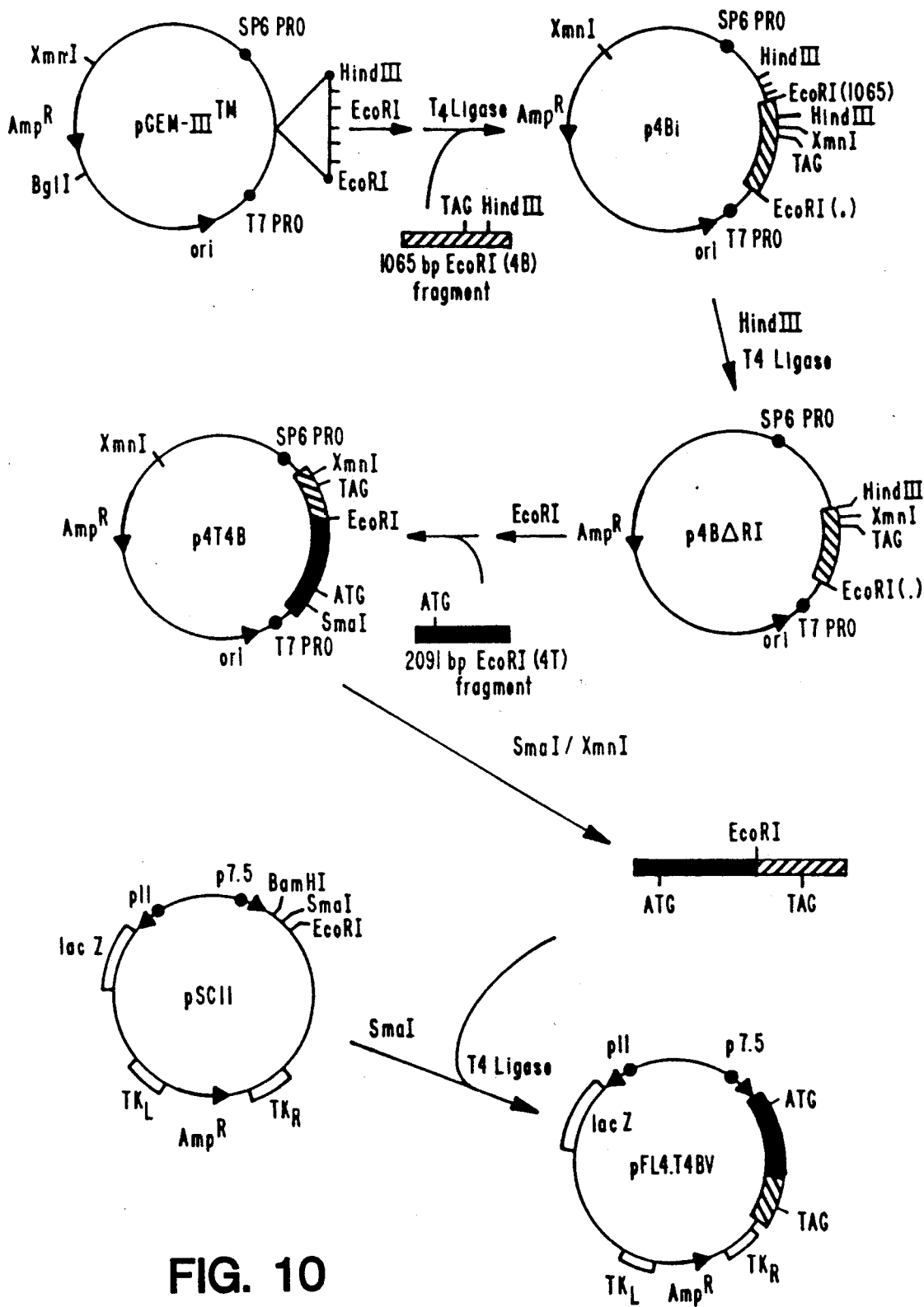
FIG. 10 shows the construction scheme for a recombinant vaccinia virus expression vector for the expression of the protein encoded by lambda APCP168i4.
Figure 11:
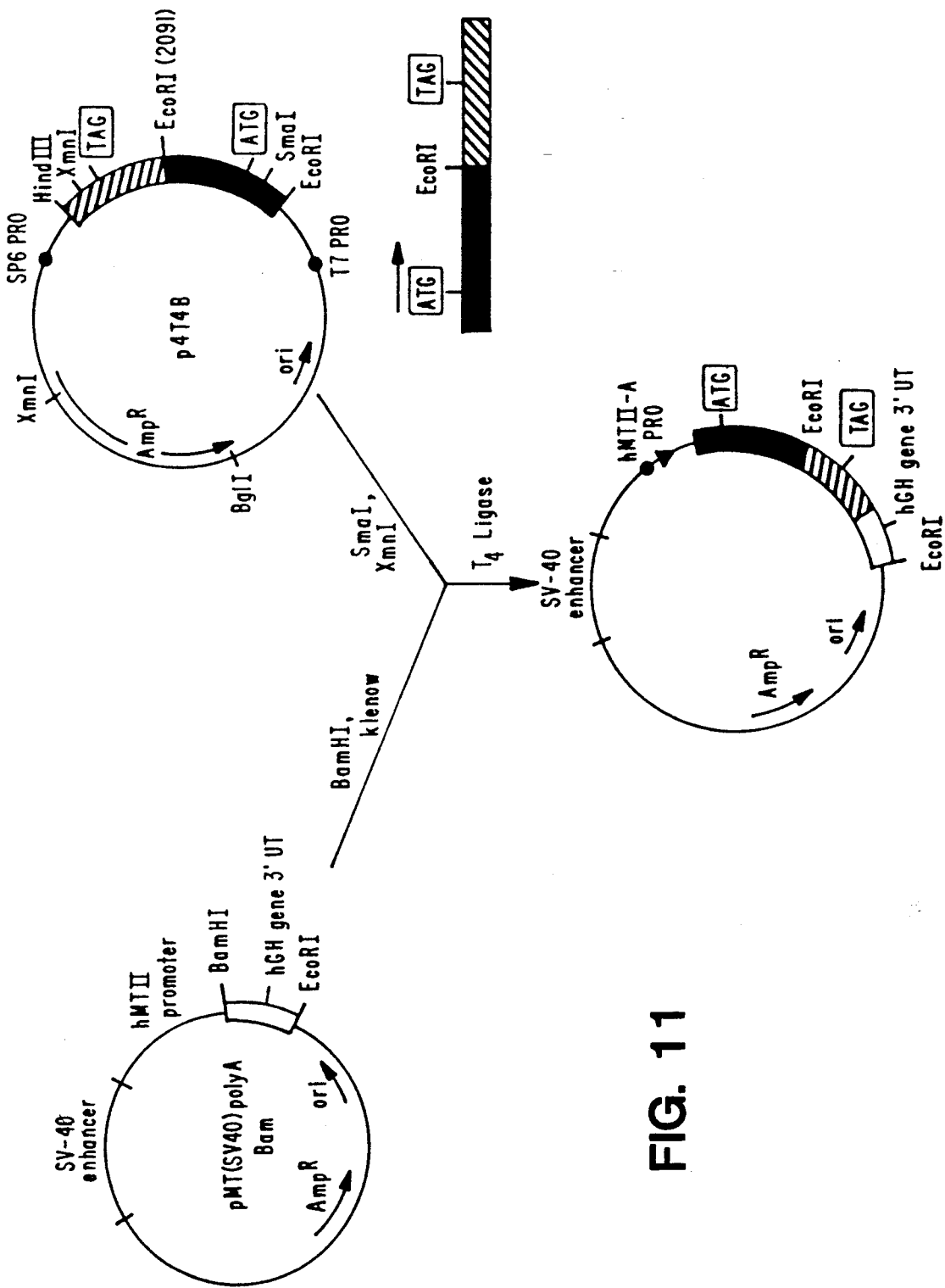
FIG. 11 shows the construction scheme for a mammalian cell expression vector for the expression of the protein encoded by lambda APCP168i4.

As used herein, "beta-amyloid core protein" means the protein described by Masters, C. L., et al., *Proc Natl Acad Sci* USA (1985) 82:4245–4249, herein referred to as "Masters, et al." This approximately 4 kD protein is defined at the amino terminus by sequence analysis as a mixture of four peptides with slightly different amino termini, the amino termini of the three smaller peptides being completely encoded by that of the largest. The first 28 amino acids of the longest form is $Asp_1$-$Ala_2$-$Glu_3$-$Phe_4$-$Arg_5$-$His_6$-$Asp_7$-$Ser_8$-$Gly_9$-$Tyr_{10}$-$Glu_{11}$-$Val_{12}$-$His_{13}$-$His_{14}$-$Gln_{15}$-$Lys_{16}$-$Leu_{17}$-$Val_{18}$-$Phe_9$-$Phe_{20}Ala_{21}$-$Glu_{22}$-$Asp_{23}$-$Val_{24}$-$Gly_{25}$-$Ser_{26}$-$Ser_{27}Ala_{28}$. The rest of the molecule is undefined by sequence analysis.

"Beta-amyloid-related protein" or "beta-amyloid-related peptide" are defined herein as those proteins containing within their sequence the beta-amyloid core protein sequence defined above or fragments of such proteins which do not necessarily include the beta-amyloid core protein sequence as defined above. As an example, this term is used to refer to the protein described by Kang, J. et al., *Nature* (1987) 325:733–736, herein referred to as "Kang, et al." which contains the betaamyloid core protein within its structure at amino acid 597 of a 695 amino acid protein. As another example, it refers to the protein encoded by lambda APCP1-68i4, shown in FIG. 1, which contains the beta-amyloid core protein within its structure at amino acid 653 of a 751 amino acid protein.

"Immunogenic beta-amyloid core peptide" or "immunogenic beta-amyloid-related peptide" refer to peptides whose amino acid sequences match those of some region of the beta-amyloid core protein or beta-amyloid-related protein, and which are capable of provoking an antibody response in an immunized animal.

"Genetic predisposition to Alzheimer's disease" refers to an identifiable genetic mutation or alteration found in the genomes of individual's with Alzheimer's disease, or those individuals destined to develop Alzheimer's disease, but not normal (nondiseased) individuals.

B. DNA Sequences

DNAs corresponding to beta-amyloid core protein or beta-amyloid-related protein sequences are useful as probes in diagnosis. Several DNAs containing sequences encoding portions of beta-amyloid-related protein sequence, and beta-amyloid core protein sequence with adjacent noncoding segments are disclosed herein. These DNA sequences in whole or in part, are thus useful in diagnosis, either as intact probes, or as fragments.

In particular, the invention includes a DNA sequence which encodes a beta-amyloid-related protein comprising the nucleotide sequence and corresponding, deduced amino acid sequence set forth in FIG. 1. This DNA sequence encodes an approximately 82,610 dalton protein containing the beta-amyloid-related core protein.

The present beta-amyloid protein cDNA sequence, set forth in FIG. 1, can be isolated from bacteriophage lambda APCP168i4. This human fibroblast cDNA clone was obtained from a cDNA library prepared in lambda gt10 using standard techniques from SV40-transformed fibroblast (SV80) cells (Todaro, G. J. et al., *Science* (1966) 153:1252–1254). The lambda gt10-SV80 library was screened with a mixture of labeled oligonucleotides. Two unique phage containing beta-amyloid-related sequences were obtained; these beta-amyloid-related sequences were subcloned into a plasmid vector and sequencing analysis revealed a sequence co-linear with the sequence encoding the Kang et al. beta-amyloid-related protein, except for the presence of a 168 basepair insert. The 168 basepair insert interrupts the codon for $Val_{289}$ of the Kang et al. sequence, resulting in the loss of this amino acid from the lambda APCP168i4 protein. The 168 basepair insert, together with the 3 basepairs gained from the interrupted $Val_{289}$ codon, encode 57 new amino acids, which are underlined in FIG. 1. Downstream of this insertion, at codon 653 of FIG. 1, lies the amino-terminal aspartate of the beta-amyloid core protein described by Masters et al. The lambda APCP168i4 clone was deposited at ATCC on Jul. 1, 1987 under the accession number 40347.

Particularly useful are those sequences which encode the 57 amino acid insert found in lambda APCP168i4, as well as sequences encoding the corresponding "junction" of the Kang et al. beta-amyloid-related protein sequence.

For example, one preferred embodiment comprises DNA sequences encoding a beta-amyloid-related protein having an amino acid sequence corresponding to residues 289 through 345 of the above-identified protein. Thus, this embodiment comprises a beta-amyloid-related protein of the amino acid sequence:

Glu Val Cys Ser Glu Gln Ala Glu Thr Gly Pro Cys Arg Ala
10

Met Ile Ser Arg Trp Tyr Phe Asp Val Thr Glu Gly Lys Cys
20

Ala Pro Phe Phe Tyr Gly Gly Cys Gly Gly Asn Arg Asn Asn
30           40

Phe Asp Thr Glu Glu Tyr Cys Met Ala Val Cys Gly Ser Ala
50

Ile.

This particular peptide, including any fragments thereof, distinguishes the present beta-amyloid-related protein from other reported forms.

In another preferred embodiment, the invention discloses a beta-amyloid-related protein having the DNA sequence and deduced amino acid sequence corresponding to amino acid residues 284-$Val_{289}$ -(Delta 289-345)-349 of the beta-amyloid-related sequence set forth in FIG. 1 (wherein Delta symbolizes a deletion of residues 289 through 345). An oligopeptide spanning this specific region would be useful to generate a protein specific diagnostic reagent to differentiate between the beta-amyloid-related protein genetic variant described by Kang et al. and the beta-amyloid-related protein of the present invention. Thus, this embodiment comprises a beta-amyloid-related protein of the amino acid sequence:

Glu Glu Val Val Arg Val Pro Thr Thr Ala
 5                              10

A smaller peptide contained within the sequence of this peptide might also be used.

Oligonucleotides specific for the 168 basepair insert and for the junctions of this region of the beta-amyloid-related protein described by Kang et al. can be synthesized and used to compare the levels of mRNA expression of these two distinct proteins. As an example, oligonucleotides specific for the 168 basepair insert, designated oligo #2734

```
            10        20         30
(CGCCGTAAAA GAATGGGGCA CACTTCCCTT 40        50         60
CAGTCACATC AAAGTACCAG CGGGAGATCA)
``` and for the "junction" region, designated oligo #2733

```
            10        20         30
(CTGCTGTTGT AGGAACTCGA ACCACCTCTT)
``` were synthesized using phosphoramidite chemistry on an Applied Biosystems DNA synthesizer.

The "junction" oligo is complementary to 15 basepairs on either side of the insert and is used to distinguish between the published beta-amyloid-related protein sequences and the lambda APCP168i4 sequences by specific hybridization conditions known in the art under which a 15 basepair perfect match is unstable, while a 30 basepair perfect match is stable. These oligonucleotides are used to screen cDNA libraries or mRNA from various sources as an assay for measuring the level of expression of a specific sequence.

Another example, described below, is a genomic sequence encoding the first 18 amino acids (19 if met is included) of the beta-amyloid protein sequence characteristic of Alzheimer's disease in neuritic plaques. The clone was obtained in lambda Charon 4A from the genomic library described by Lawn, R. M., et al., *Cell* (1978) 15:1157-1174 and has been partially sequenced, as shown in FIG. 2. As seen, the sequenced portion of the genomic clone includes a 57 base pair segment which encodes the amino acids 1-18 of the previously reported beta-amyloid core protein and a methionine immediately preceding. Downstream of the amino acid 18 codon, the genomic sequence diverges in codon sequence from that expected from the reported amino acid sequence of betaamyloid core protein. By reference to the protein encoded by the sequence of FIG. 4, and by inspection of the sequences flanking this region using knowledge known in the art, this divergence is likely to be an intron sequence. This clone, designated lambda SM2, was deposited at ATCC on Nov. 13, 1986.

A HindIII/RsaI probe derived from the genomic clone (see FIG. 2) was used as a probe to isolate, according to standard procedures, cDNA fragments from a cDNA library constructed in lambda gt10 from temporal and parietal cortical tissue of a normal human brain (the individual was a 55 year old man who died of myocardial infarction). The three cDNA clones which were isolated were sequenced conventionally, and matched with amino acid sequences in each of the three possible reading frames to identify regions coding for beta-amyloid-related proteins. One of the clones, designated lambda SM2W4, contains a 3'-end terminal sequence which encodes the Asp Ala Glu Phe amino acids at the 5'-end of beta-amyloid-core protein, as seen in FIG. 3, which shows the complete base sequence of the clone. The $Asp_1$ codon is immediately preceded by a methionine codon. A second clone, designated lambda SM2W3, contains a 5' region segment which has a 6 bp overlap with the 3' end of the lambda SM2W4 clone (an EcoRI restriction site), encoding amino acids 3 and 4 of the beta-amyloid core protein, and an additional 95 codons which encode the remainder of a beta-amyloid-related protein. The DNA sequence for the 100 amino acid protein (including Met) encoded in lambda SM2W4 and lambda SM2W3 is shown in FIG. 5. It is, of course, understood that the methionine is probably processed in vivo, and that the beta-amyloid-related protein represented in this figure may thus be a 99 amino acid sequence.

A third cDNA clone encodes a portion of a beta-amyloid-related protein which differs from lambda SM2W3 in the region shown by 15 nucleotide differences and 4 amino acid differences in the region of amino acids 3-44 of FIG. 5. The DNA sequence and deduced amino acid sequence for this clone, designated lambda SM2W9 are given in FIG. 6. A comparison with lambda SM2W3 is given in FIG. 7.

The lambda SM2W4, lambda SM2W3, lambda SM2W9, and lambda APCP168i4 clones have been deposited with the American Type Culture Collection, Rock Lawn, MD and have ATCC Nos. 40299, 40300, 40304 and 40347, respectively.

C. Protein Production

The four cDNA clones above permit construction of coding sequences which may be expressed to obtain a complete beta-amyloid-related protein, an 100 amino acid beta-amyloid-related protein containing the amino-terminal sequences reported for beta-amyloid core protein, and other desired proteins. These sequences can be inserted in a suitable expression vector for production of protein. Details of the method of constructing a DNA subsequence of FIG. 1 and insertion of this sequence into a bacterial expression vector is provided in Example 2.

Briefly, an *E. coli* expression vector, designated pAPCP118-3, was constructed for the expression of a fusion protein consisting of amino acid residues 655 to 751 set forth in FIG. 1. The construction of pAPCP118-3 was accomplished by joining the following three fragments: (1) a plasmid backbone (consisting of pBR322 replication functions, an ampicillin resistance gene, the tryptophan promoter and operator, a ribosome binding site, DNA encoding the seven amino terminal codons of the beta-galactosidase structural gene followed by six threonine residues, and transcription termination signals); (2) an EcoRI-HaeII fragment encoding amino acid residues 655-728 of the FIG. 1 sequence; and (3) a synthetic fragment encoding amino acid residues 729-751 of the FIG. 1 sequence, followed by a stop codon.

The resulting vector was used to transform *E. coli* W3110 and expression of the fusion protein was induced by reducing the tryptophan concentration followed by the addition of 3-beta-indoleacrylic acid. The resulting protein can be purified using conventional purification techniques and the resulting purified material is available for use in the production of antibodies for diagnostic assays.

The complete coding sequence of the beta-amyloid-related protein set forth in FIG. 1 was subcloned in two fragments from the deposited lambda APCP168i4 clone and inserted into pSC11, a vaccinia virus expression vector. The construction of the resulting vector, pFL4T4BV, is illustrated in FIG. 10. Briefly, an approximately 1.06 kilobase (kb) EcoRI fragment, spanning amino acid residues 655-751 of the protein illustrated in FIG. 1, was cloned into EcoRI-digested plasmid pGEM-3 TM (available from Promega Biotec) to create an intermediate vector designated p4BI. Subsequently p4BI was digested with HindIII to remove much of the 3'-noncoding sequence of the beta-amyloid-related sequence. The resulting vector p4B DELTA RI was digested with EcoRI and treated with calf intestinal alkaline phosphatase prior to ligation to the 2088 bp EcoRI fragment derived from lambda APCP168i4 to form p4T4B. This plasmid was digested with SmaI and XmnI to generate a 2678 bp fragment spanning the complete protein encoding sequence set forth in FIG. 1.

The gene encoded by this SmaI-XmnI fragment was inserted into a well-known vaccinia viral vector, pSC11, for subsequent expression of the beta-amyloid-related protein in CV-1 monkey kidney cells using a eucaryotic transient expression system as described by Cochran, M. A., et al. (1985) *Proc Natl Acad Sci USA* 82: 19-23. More commonly, this vector is used for in vivo protein and antibody production in animals after its sequences have been inserted into the vaccinia virus genome (see "Antibody Production" section below).

Similarly, mammalian vectors can be utilized for expression of the beta-amyloid core protein or beta-amyloid-related proteins described herein. For example, plasmid phGH-SV (10) (a plasmid described in EPA 217,822, published Apr. 15, 1987, and incorporated herein by reference) contains a pUC8 plasmid backbone, hMT-IIa gene promoter and regulator elements, SV-40 DNA promoter and enhancer elements, and the coding portions of the hGH gene and 3' regulatory sequences. This plasmid can be digested with BamHI and SmaI and treated with BamHI linkers to delete the human growth hormone protein encoding sequence and leaving the 3'-noncoding sequences and regulatory elements attached to the plasmid backbone. This approximately 5100 base pair DNA piece is gel purified and ligated to BamHI linkers. Digestion with BamHI, repurification of the DNA fragment and subsequent ligation result in a plasmid designated pMTSV40 polyA Bam which contains the structural and regulatory elements comprising a mammalian cell expression vector. After BamHI digestion of pMTSV40 polyA Bam and repair in the presence of DNA polymerase I and all four dNTPs, this vector is available for insertion of the approximately 2678 bp SmaIXmnI restriction fragment of plasmid p4T4B. The resulting vector can then be used for efficient protein expression in CHO cells as described in Example 4.

In addition, the sequence information from the lambda SM2W4 clone, illustrated in FIG. 3, combined with the sequences present in the lambda SM2W3 clone, may be used to construct a mammalian cell expression vector encoding the protein described in FIG. 5.

In the cases of protein production described above, the transformed cells are screened for production of the resulting beta-amyloid-related protein using anti-beta-amyloid antibody prepared as described below.

D. Antibody Preparation

Antibodies specific against beta-amyloid core protein and beta-amyloid-related proteins are prepared by known procedures. As an example using synthetic peptides, typically the protein sequence is analyzed for regions of at least about 10 amino acids long which have predominantly polar and/or charged amino acid residues to identify favorable immunogenic regions.

As another example, the DNA sequence shown in FIG. 1 can be used to design oligopeptides which are specific to the inserted sequence in lambda APCP168i4, as well as the corresponding junction of this insert to the beta-amyloid-related protein described by Kang et al. For example, an oligopeptide spanning the inserted junction such as Glu-Glu-Val-Val-Arg-Val-Pro-Thr-Thr-Ala may be used to immunize animals to produce a specific antisera against this region of the protein described by Kang et al. Inspection of the Kang et al. sequence in the absence of knowledge of the lambda APCP168i4 sequence, would not provide the information necessary to identify this peptide as a valuable reagent by any method known in the art. As another example, oligopeptides designed to represent sequences present in the 168 basepair insert region could be used in a similar manner to generate antisera against this unique region of the APCP168i4 protein. Thus, the regions identified as favorable for immunogenicity are synthesized by conventional peptide synthetic methods, and coupled covalently to a suitable carrier protein, such as keyhole limpid hemocyanin. Antibodies are raised against the peptide/protein conjugate in rabbits or the like by conventional methods. The presence of antibody in immunized animals is detected by standard methods, such as immunoreactivity to the immunizing synthetic peptide affixed to a microtiter plate, followed by ELISA.

Another method of antibody production uses the bacterially produced beta-amyloid-related fusion protein of example 2 as the immunogen. The immunogenicity of this protein is shown by the immunoreactivity of the antisera to the bacterially produced fusion protein.

Yet another method of antibody production relies on the inoculation of the host animal with a live recombinant vaccinia virus encoding beta-amyloid-related protein, such recombinant viruses being generated by established techniques involving recombination between wild-type vaccinia virus and the vectors derived from pSCl1, such as pFL4T4BV, described herein. These antibodies can then be used in the diagnostic assays described below.

A panel of antibodies which are specific against peptides derived from different regions of the beta-amyloid-related protein, such as the 57 amino acid insert of lambda APCP168i4, are further analyzed for immunoreactivity of beta-amyloid-related proteins present in the serum or cerebral spinal fluid of patients with Alzheimer's disease, to identify antibodies suitable for a diagnostic assay for Alzheimer's disease, as discussed below.

E. Diagnostic and Prognostic Methods

The DNA sequences described in FIGS. 3, 4, and 6 for beta-amyloid-related protein are primarily derived from an apparently normal advanced-age male showing no signs of Alzheimer's disease at the time of death. The lambda APCP168i4 sequence described in FIG. 1 for another beta-amyloid-related protein is derived from cultured fibroblast cells. These sequences provide a standard for identifying mutations in genomic sequences which are found in individuals with Alzheimer's disease, and which are therefore likely to be associated with a predisposition to the disease.

1. Prognostic Methods. Assays are used to determine an individual's genetic predisposition to Alzheimer's disease. These tests use the DNA sequences of the present invention in a comparative study with samples of the patient s DNA to define polymorphisms in the region of the chromosome containing the beta-amyloid gene. Alternatively or concurrently, the DNA sequences of the present invention can be used in nucleic acid hybridization analysis to define alterations, which alterations are meant to include additions, deletions, mutations or substitutions, in the DNA or RNA encoding beta-amyloid-related proteins.

Alterations in the beta-amyloid-related protein sequences which correlate with Alzheimer's disease can be assayed by a differential probe binding method. Under appropriate hybridization conditions, known in the art, the oligonucleotide probes will bind to completely complementary sequences, but not to closely related but altered sequences.

In one assay method, nucleic acid samples prepared from the test subject are hybridized with each probe, under the defined hybridization conditions, and examined for binding to specific oligonucleotides. Alterations, and thus predisposition to Alzheimer's disease, are confirmed by binding one probe, but not to the other probe. The probe-binding method, as it has been applied to other genetic diseases, is described in Conner, B. J., et al., *Proc Nat Acad Sci* (USA) 80:278–282 (1983).

Alternatively, probes derived from the genomic or cDNA sequences described above may be used to identify restriction fragment length polymorphisms which are associated with a genetic predisposition to Alzheimer's disease. Initially the probes are used to identify restriction site fragment lengths from both normal and diseased genomic digest samples. Changes in restriction fragment lengths which correlate with Alzheimer's disease are then applied to genetic screening, by standard methods. That is, test subject genomic material is digested with the restriction enzyme(s) of interest, and the fragment pattern on Southern blotting is determined with the labeled probe.

2. Diagnostic Methods. In various other clinical amyloidosis, the amyloidogenic peptides are variants of normally expressed gene products. These peptides have been altered either by aberrant proteolytic processing or by genetic lesions yielding an alteration in the primary amino acid sequences. There are known amyloidosis, such as Familial Amyloid Polyneuropathy (FAP), in which a mixture of the normal precursor and the amyloidogenic variant coexist within the circulation. An aberrant tissue-distribution for the expression of the aberrant gene product, or some other alteration in its level of expression, its sequence, or its processing in Alzheimer's disease could have significance in terms of the etiology of amyloid deposition.

A first diagnostic test which utilizes the materials of the invention is a direct antibody assay for the increase or decrease of beta-amyloid core protein or beta-amyloid-related proteins in Alzheimer's individuals relative to normal individuals. In this method, antibodies obtained as described above are screened for specific with proteins from individuals known to immunoreactivity with proteins from individuals known to have Alzheimer's disease. The presence of immunoreactive serum proteins is determined by standard immunoassay techniques, such as solid-phase ELISA techniques.

The body sample which is assayed for the presence of beta-amyloid core protein or beta-amyloid-related protein is, for example, serum or cerebral spinal fluid. For instance, in hereditary cerebral hemorrhage with amyloidosis, a disorder wherein the amyloid is generated from the gamma-trace precursor, the precursor can be detected in cerebrospinal fluid using an immunoassay. The levels of the precursor are reduced in the patients having the disease, leading to the conclusion that it is used up during the formation of the deposits. The precursor is made in the brain, and hence the cerebrospinal fluid is the appropriate sample.

In another diagnostic test, DNA encoding beta-amyloid-related protein is directly useful as a probe to detect an increase or decrease in synthesis of mRNAs encoding beta-amyloid-related proteins in the appropriate target cells by virtue of its ability to hybridize to the appropriate mRNA. An example showing the utility of this method is given in Example 5 below.

A third diagnostic assay permits the detection of antibodies against the amyloid protein in patient's serum using such standard ELISA techniques wherein the purified recombinant amyloid protein or synthetic peptide is bound to the solid support.

F. Therapeutic Methods.

The invention also provides for improved therapeutic treatments for Alzheimer's disease. One therapeutic treatment is suggested in the sequence of the protein encoded by the 168 bp insert in lambda APCP168i4. Using methods well known in the art such as the use of computer programs which search protein databases, to compare the protein relatedness of one protein to another, the protein encoded by the 168 bp insert was found to be highly homologous to a family of proteins known as Kunitz basic protease inhibitors. The level of relatedness of the insert protein segment to three members of the family is shown in FIG. 13, where the symbol (:) indicates an identity between the two sequences compared and the symbol (.) indicates the substitution of an amino acid with similar chemical properties. The insert sequence, depicted by the one-letter amino acid code as EVCS ... GSAI is shown to be related to a high degree over its entire length to all members of the family (only three are shown as an example). The comparisons shown are to: (1) a human trypsin inhibitor, a secreted plasma protein which inhibits trypsin, plasmin and lysosomal granulocytic elastase (Wachter, E., and Hochstrasser, K. (1981) *Hoppe-Seyler's Z Physiol Chem* 362:1351–1355; Morii, M., and Travis, J. (1985) *Biol Chem Hoppe-Seyler* 366:19–21; (2) a bovine trypsin inhibitor which inhibits trypsin, chymotrypsin, elastases and plasmin (Hochstrasser, K. and Wachter, E., (1983) *Hoppe-Seyler's Z Physiol Chem* 364:1679–1687; Hochstrasser, K., et al. (1983), *HoppeSeyler's Z Physiol Chem* 364:1689–1696; and (3) a bovine serum basic protease inhibitor (and its precursor) which inhibits trypsin, kallikrein, chymotrypsin, and plasmin (Anderson, S. and Kingston, I. B. (1983) *Proc Nat Acad Sci* (USA) 80:6838–6842. Based on this level of relatedness to the 168 bp insert protein sequence, one interpretation is that this region of the lambda APCP168i4 protein has a function as a protease inhibitor in vivo. While not wishing to be bound by this interpretation, it does suggest that a protease inhibitor based on the sequence of the 168 bp insert protein or a fragment thereof could be useful as a therapeutic reagent for Alzheimer's disease. This or other protease inhibitors, peptidic or non-peptidic, could be used to treat or prevent Alzheimer's disease by a mechanism such as preventing the formation of neuritic plaques. One method of administration might involve nasal delivery of such a peptide (as the blood-brain barrier is known to be more open immediately behind the nasal cavity). Nasal delivery could be accomplished by formulating the protease inhibitor peptide with excipient and an effective amount of an adjuvant, such as the fusidic acid derivatives or a polyoxyethylene ether at a concentration of 0.1-10% (w/w). Stabilizers or disinfectants could optionally be added. The amount of peptide would vary, depending on its efficacy and bioavailability, but could range from 0.1-25% (w/w). Administration would occur by spraying from 10-100 ul of the solution into each side of the nose from 1-4 times a day, although dosing could also be more or less frequent. Other modes of delivery include a solution of inhibitor in a pharmaceutically acceptable excipient where the inhibitor is 0.1-25% (w/w) and where the inhibitor is administered by injection into the bloodstream or into the spinal column, or directly onto the brain. If the inhibitor is non-peptidic, oral dosing may be possible.

G. Methods and Materials

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Hosts and Control Sequences

Both procaryotic and eucaryotic systems may be used to express the beta-amyloid core and beta-amyloid-related sequences; procaryotic hosts are, of course, the most convenient for cloning procedures. Procaryotes most frequently are represented by various strains of *E. coli;* however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al., *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al., *Nature* (1977) 198:1056) and the tryptophan (trp) promoter system (Goeddel, et al. *Nucleic Acids Res* (1980) 8:4057) and the lambda derived $P_L$ promoter and N-gene ribosome binding site (Shimatake, et al., *Nature* (1981) 292:128).

In addition to bacteria, eucaryotic microbes, such as yeast, may also be used as hosts. Laboratory strains of *Saccharomyces cerevisiae,* Baker's yeast, are most used although a number of other strains or species are commonly available. Vectors employing, for example, the 2u origin of replication of Broach, J. R., *Meth Enz* (1983) 101:307, or other yeast compatible origins of replication (see, for example, Stinchcomb, et al., *Nature* (1979) 282:39, Tschumper, G., et al., *Gene* (1980) 10:157 and Clarke, L, et al., *Meth Enz* (1983) 101:300) may be used. Control sequences for yeast vectors include promoters for the synthesis of glycolytic enzymes (Hess, et al., *J Adv Enzyme Reg* (1968) 7:149; Holland, et al., *Biochemistry* (1978) 17:4900). Additional promoters known in the art include the promoter for 3-phosphoglycerate kinase (Hitzeman, et al., *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al., U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al., *Nature* (1978) 273:113), or other viral promoters such as those derived from polyoma, Adenovirus 2, bovine papilloma virus, or avian sarcoma viruses. The controllable promoter, hMTII (Karin, M., et al., *Nature,* (1982) 299:797-802) may also be used. General aspects of mammalian cell host system transformations have been described by Axel (supra). It now appears, also that "enhancer" regions are important in optimizing expression; these are, generally, sequences found upstream or downstream of the promoter region in noncoding DNA regions. Origins of replication may be obtained, if needed, from viral sources. However, integration into the chromosome is a common mechanism for DNA replication in eucaryotes.

Transformations

Depending on the host cell used, transformation is done using standard techniques appropriate to such cells. The calcium treatment employing calcium chloride, as described by Cohen, S. N., *Proc Natl Acad Sci (USA)* (1972) 69:2110, or the RbCl$_2$ method described in Maniatis, et al., *Molecular Cloning: A Laboratory Manual* (1982) Cold Spring Harbor Press, p. 254 and Hanahan, D., *J Mol Biol* (1983) 166:557-580 may be used for procaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al., *Cell* (1979) 16:777-785 may be used. Transformations into yeast may be carried out according to the method of Beggs, J. D., *Nature* (1978) 275:104-109 or of Hinnen, A., et al., *Proc Natl Acad Sci (USA)* (1978) 75:1929.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and relegated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; Jay, Ernest, *J Biol Chem* (1984) 259:6311.

Synthetic oligonucleotides are prepared by either the phosphotriester method as described by Edge, et al., *Nature* (supra) and Duckworth, et al., *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM MgCl$_2$, 5 mM dithiothreitol, 1-2 mM ATP, 1.7 pmoles lambda 32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 ug of plasmid or DNA sequence is cleaved by one unit of enzyme in about 20 ul of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15-50 ul volumes under the following standard conditions and temperatures: for example, 20 mM Tris-HCl pH 7.5, 10 mM MgCl$_2$, 10 mM DTT, 33 ug/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 ug/ml total DNA concentrations (5-100 nM total end concentration). Intermolecular blunt end ligations are performed at 1 uM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per ug of vector at 60° C. for about one hour. In order to recover the nucleic acid fragments, the preparation is extracted with phenol/chloroform and ethanol precipitated. Alternatively, relegation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487-6500 and Adelman, J. P., et al., *DNA* (1983) 2:183-193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Verification of Construction

In the constructions set forth below, correct ligations for plasmid construction are confirmed by first transforming *E. coli* strain MC1061 obtained from Dr. M. Casadaban (Casadaban, M., et al., *J Mol Biol* (1980) 138:179-207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al., *Proc Natl Acad Sci (USA)* (1969) 62:1159, optionally following chloramphenicol amplification (Clewell, D. B., *J Bacteriol* (1972) 110:667). Several mini DNA preps are commonly used, e.g., Holmes, D. S., et al., *Anal Biochem* (1981) 114:193-197 and Birnboim, H. C., et al., *Nucleic Acids Res* (1979) 7:1513-1523. The isolated DNA is analyzed by restriction and/or sequenced by the dideoxy nucleotide method of Sanger, F., et al., *Proc Natl Acad Sci (USA)* (1977) 74:5463 as further described by Messing, et al., *Nucleic Acids Res* (1981) 9:309, or by the method of Maxam, et al., *Methods in Enzymology* (1980) 65:499.

The invention will be further described by the following examples. These are provided only to illustrate embodiments of the invention and are not to be construed as limitations on the invention's scope.

EXAMPLE 1

Isolation of a Genomic Clone and cDNA Clones Encoding Beta-amyloid Core Protein and Beta-amyloid-related Proteins A human genomic library in Charon 4A lambda-phage was screened using a sixfold degenerate 38 mer probe corresponding to the first 13 amino acids of the 28 amino acid sequence N-terminal sequence. This probe,

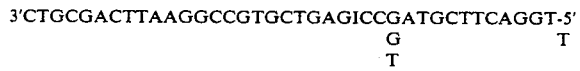

wherein I is inosine, when used to screen the human genomic library yielded a strongly hybridizing colony designated lambda SM2. Lambda SM2 DNA was isolated and partially sequenced with the results shown in FIG. 2. The sequenced portion is only a small fraction of the approximately 10-20 kb insert in the phage isolated from the genomic library.

A probe was constructed from the HindIII/RsaI fragment representing approximately positions 201-294. The genomic probe was used to screen a cDNA library prepared in lambda gt10 using standard techniques from brain tissue of a 55 year old man with no evidence of Alzheimer's disease. The three clones designated lambda SM2W4, lambda SM2W3 and lambda SM2W9 were identified.

EXAMPLE 2

The genomic and cDNA sequences described above can be used to prepare recombinant protein in an efficient expression system. Genomic DNA can be utilized in cells, such as mammalian cells, capable of processing introns. Bacterial cells can be utilized for expression of cDNA sequences.

Bacterial Expression of Beta-Amyloid-Related Protein (655-751) and Production of Antisera A. Construction of plasmid pAPCP118-3

Construction of an *E. coli* expression vector for human beta-amyloid-related protein (655-751) required the joining of three DNA fragments: (1) a plasmid backbone (consisting of replication functions, ampicillin resistance gene, tryptophan promoter/operator, ribosome binding site, DNA encoding the amino terminus of *E. coli* beta-galactosidase (7 amino acids) followed by six threonine residues, and transcription termination signals), (2) a fragment of the beta-amyloid-related DNA encoding amino acids 655-728, of FIG. 1 and (3) a synthetic fragment of the beta-amyloid-related DNA encoding amino acids 729-751 of FIG. 1 and the stop codon UAA.

Figure 14A:
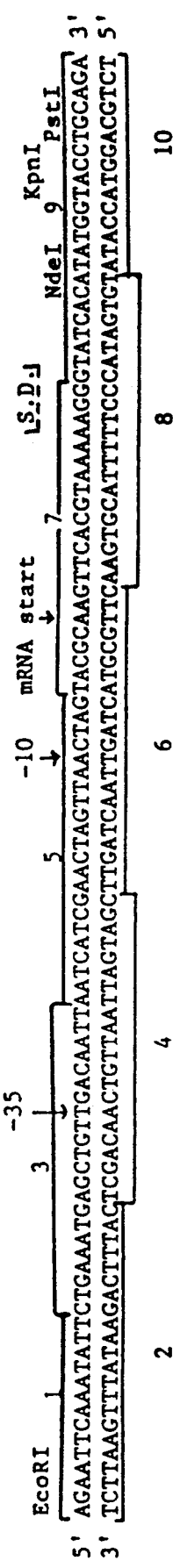
FIG. 14 shows the construction of a synthetic tryptophan operand promoter and operator regulatory sequence, and a restriction site map of plasmid pTRP233.
Figure 14B:
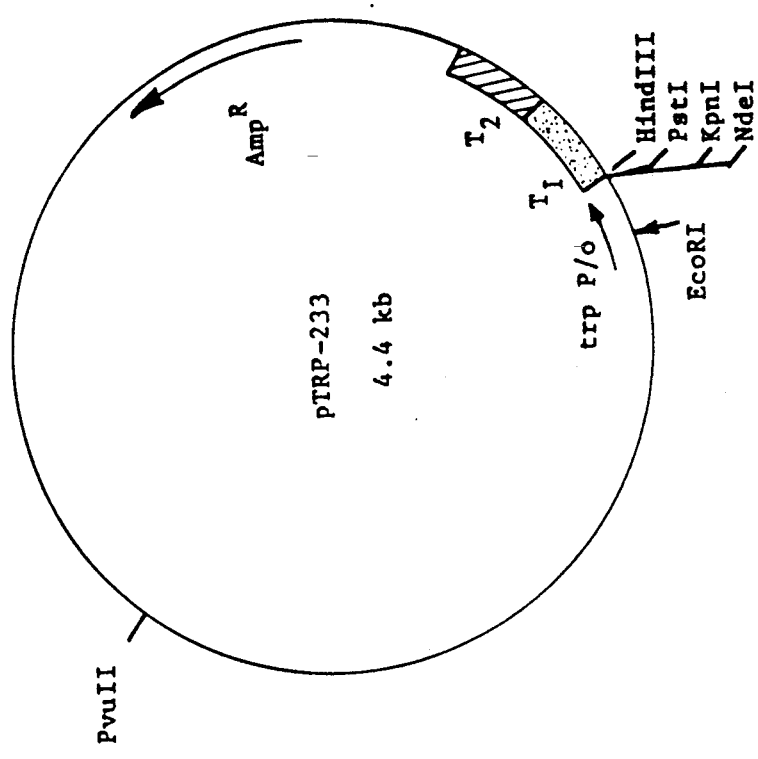

The plasmid backbone referred to above is derived from pTRP83-1. Plasmid pTRP83-1 is a bacterial expression plasmid which was constructed in the following manner:

Construction of the Synthetic Tryptophan Operand Promoter and Operator Regulatory Sequence The ten oligodeoxynucleotides shown in FIG. 14 were synthesized by the phosphotriester method and purified. 500 pmole of each oligodeoxynucleotide except 1 and 10 were phosphorylated individually in 20 ul containing 60 mM Tris-HCl, pH 8, 15 mM DTT, 10 mM MgCl$_2$, 20 uCi of [lambda-$^{32}$P]-ATP and 20 units of polynucleotide kinase (P/L Biochemicals) for 30 min. at 37° C. This was followed by the addition of 10 ul containing 60 mM Tris-HCl, pH 8, 15 mM DTT, 10 mM MgCl$_2$, 1.5 mM ATP and 20 additional units of polynucleotide kinase followed by another 30 min incubation at 37° C. Following incubation the samples were incubated at 100° C. for 5 min. 500 pmole of oligodeoxynucleotides 1 and 10 were diluted to 30 ul in the above buffer without ATP.

16.7 pmole of each oligodeoxynucleotide constituting a double stranded pair (e.g. oligodeoxynucleotides 1 and 2, 3 and 4 etc. FIG. 14 were mixed and incubated at 90° C. for 2 min followed by slow cooling to room temperature. Each pair was then combined with the others in the construction and extracted with phenol/chloroform followed by ethanol precipitation. The oligodeoxynucleotide pairs were reconstituted in 30 ul containing 5 mM Tris-HCl, pH 8, 10 mM MgCl$_2$, 20 mM DTT, heated to 50° C. for 10 min and allowed to cool to room temperature followed by the addition of ATP to a final concentration of 0.5 mM. 800 units of T4 DNA ligase were then added and the mixture incubated at 12.5° C. for 12-16 hours.

The ligation mixture was extracted with phenol/chloroform and the DNA ethanol precipitated. The dried DNA was reconstituted in 30 ul and digested with EcoRI and PstI for 1 hour at 37° C. The mixture was extracted with phenol/chloroform and ethanol precipitated followed by separation of the various double stranded DNA segments by electrophoresis on an 8% polyacrylamide gel, according to the method of Laemmli et al., *Nature* (1970) 227:680. The DNA fragments were visualized by wet gel autoradiography and a band corresponding to approximately 100 bp in length was cut out and eluted overnight as described. The excised synthetic DNA fragment was ligated to plasmids M13-mp8 or M13-mp9 (Messing and Vieira, (1982) *Gene* 19:259-268) similarly digested with EcoRI and PstI, and submitted to dideoxynucleotide sequence analysis to confirm the designed sequence. This designed sequence contains the promoter (-35 and -10 regions) and operator regions of the tryptophan operand (trp) as well as the ribosome binding region of the tryptophan operand leader peptide. Analogous sequences to that shown in FIG. 14 have been proven to be useful in the expression of heterologous proteins in *E. coli* (Hallewell, R. A., and Emtage, S., (1980) *Gene* 9:27-47, Ikehara, M., et al., *Proc Natl Acad Sci (USA)* (1984) 81:5956-5960).

2. Construction of the Synthetic trp Promoter/Operator Containing Plasmid pTRP233

Plasmid pKK233-2 (Amann, E. and Brosius, J. (1985) *Gene* 40:183 was digested to completion with NdeI and the ends were made blunt with 5 units of *E. coli* polymerase I, Klenow fragment (Boehringer-Mannheim, Inc.) and the addition of all four dNTPs to 50 uM. This was incubated at 25° C. for 20 min. Following phenol/chloroform extraction and ethanol precipitation, the NdeI-digested DNA was ligated and transformed into *E. coli* (Nakamura, K. et al. (1982) J Mol Appl Genet 1:289-299). The resulting plasmid lacking the NdeI site was designated pKK-233-2Nde.

Twenty nanograms of plasmid pKK-233-2-Nde was digested to completion with EcoRI and PstI followed by calf intestinal phosphatase treatment. Fifty nanograms of the synthetic trp promoter/operator sequence obtained from M13 RF, by digesting with EcoRI and PstI, were mixed with ten nanograms of EcoRI and PstI-digested pKK-233-2-Nde and ligated with T4-DNA ligase, followed by transformation into *E. coli* JA221 lpp-/I,lacI. Transformants were screened for the presence of plasmid DNA containing the 100 bp EcoRI-PstI synthetic trp promoter/operator; the correct plasmid was then isolated and designated pTRP233.

pTRP233 was digested with EcoRI, the ends blunted with Klenow, and ligated to remove the EcoRI restriction site. The plasmid was next digested with NdeI and HindIII and an NdeI-EcoRI-HindIII fragment encoding beta-gal-(thr)6 between the NdeI and EcoRI sites was inserted to create plasmid pTRP83-1.

Plasmid pTRP83-1 was then digested with EcoRI and HindIII restriction endonucleases and the digest was electrophoresed in a 0.6% agarose gel (Maniatis, T. et al. at pp. 157-160). The large fragment containing the plasmid backbone was eluted from the gel. Next, the EcoRI fragment from plasmid pAPCP113-3 containing beta-amyloid-related sequences derived from lambda SM2W3 (corresponding to amino acids 655-751 of FIG. 1 and 500 bp of 3'-untranslated sequences) was digested with HaeII restriction endonuclease and electrophoresed in a 12% polyacrylamide gel. The approximately 230 bp EcoRI-HaeII fragment (containing beta-amyloid-related sequences encoding amino acids 655-728 was eluted. The remaining portion of the beta-amyloid-related sequences of FIG. 1 encoding amino acids from 728-751 were prepared using the six oligodeoxynucleotides illustrated in FIG. 9. 500 pmole of each oligodeoxynucleotide except for 1 and 6 were phosphorylated individually. 167 pmole of each oligodeoxynucleotide constituting a pair (e.g. 1 and 2, 2 and 3, etc.) were mixed and incubated at 90° C. for 2 min followed by slow cooling to room temperature. Each pair was then combined with the others and extracted with phenol/chloroform followed by ethanol precipitation. The pairs were reconstituted in 30 ul containing 5 mM TrisHCl, pH 8, 10 mM $MgCl_2$, 20 mM DTT, heated to 50° C. for 10 min, and allowed to cool to room temperature. ATP was added to a final concentration of 0.5 mM, 800 units of T4 DNA ligase was added and the mixture incubated at 12° C. for 12-16 hr. The ligation was electrophoresed in a 12% polyacrylamide gel and the 79 bp HaeII-HindIII synthetic fragment was eluted.

The EcoRI-HindIII plasmid backbone of pTRP83-1, the approximately 230 bp EcoRI-HaeII beta-amyloid cDNA fragment, and the 79 bp synthetic HaeII-HindIII beta-amyloid fragment were ligated at 12° C. for 12-16 hr. *E. coli* strain MC1061 was transformed with the ligation mixture (Maniatis, T. et al., pp. 250-251) and the resulting ampicillin resistant colonies were grown overnight in 1 ml of L broth supplemented with 100 ug/ml ampicillin sulfate. Plasmid DNA was prepared by the alkaline lysis method (Maniatis et al., pp. 368-369). Plasmids were screened for the correct inserts by digestion with EcoRI and HindIII. A plasmid releasing an approximately 300 bp EcoRI-HindIII fragment was designated pAPCP118-3.

B. Expression of beta-amyloid-related Fusion Polypeptide (655-751)

The plasmid pAPCP118-3 expresses a 110 amino acid beta-galactosidase-threonine-beta-amyloid-related fusion protein under the control of the *E. coli* tryptophan promoter/operator. *E. coli* strain W3110 was transformed with plasmid pAPCP118-3 and one of the resulting ampicillin resistant colonies was grown for 12-16 hr at 37° C. in media containing M9 minimal salts (Miller, J., Experiments in Molecular Genetics, Cold Spring Harbor Laboratory, Cold Spring Harbor, N.Y.) supplemented with glucose (0.4%), thiamine (2 ug/ml), $MgSO_4*7H_2O$ (200 ug/ml), tryptophan (40 ug/ml), casamino acids (0.5%), and ampicillin (100 ug/ml). Expression was induced by dilution of the culture 100-fold into new media with reduced tryptophan (4 ug/ml) for 2 hr followed by the addition of 3-beta-indoleacrylic acid at a final concentration of 25 ug/ml. Expression of beta-gal-thr-beta-amyloid (655-751) fusion protein occurs at the level of 10-20% of total cell protein, and is present in the form of inclusion bodies which can be visualized by phase contrast microscopy (1000×magnification). The cells were harvested 6 hr after the addition of the 3-beta-indoleacrylic acid by centrifugation, washed with 10 mM Tris-HCl, pH 7.5, and the cell pellet frozen at −20° C.

Purification of Beta-gal-thr-Beta-amyloid (655-751) Fusion Protein for Preparation of Antiserum A cell pellet from 500 ml of culture was resuspended in 40 ml of 10 mM Tris-HCl, pH 7.5, 0.6M NaCl, and incubated with 8 mg of lysozyme and the protease inhibitors phenylmethylsulfonylfluoride (PMSF) and aprotinin (0.5 mM and 25 ug/ml respectively) for 10 min at 4° C. Solutions of the two detergents, sodium deoxycholate (480 ul of 10% solution) and NP-40 (240 ul of 20% solution), were then added for an additional 10 min incubation at 4° C. The cell pellet was sonicated to disrupt cells and free inclusion bodies. RNAse (10 ug/ml) and DNAse (10 ug/ml) were added and the mixture stirred for 30 min at room temperature to digest RNA and DNA. The inclusion bodies (and some cell debris) were collected by centrifugation for 10 min at 5000 rpm (SA600 rotor). The supernatant was discarded and the pellet boiled in protein gel sample buffer for 20 min to solubilize the fusion protein. The fusion protein was then purified by electrophoresis in 12% SDS/polyacrylamide gels (Laemmli, U. K., *Nature* (1970), 227:680). The edges of each gel were removed and stained with Coomassie blue to visualize the 15 kilodalton (kD) fusion protein. They were then realigned with the gel so that the region of the gel containing the fusion protein could be excised. The polyacrylamide was then crushed through a series of needles (16 gauge down to 22 gauge) with the addition of physiological saline to keep the polyacrylamide moist. The polyacrylamide/fusion protein crush was mixed with adjuvant [RIBI(-RAS)] just prior to immunization of the rabbits. Approximately 150–200 ug of fusion protein was administered per animal for the first immunization. Subsequent immunizations use 50–100 ug of fusion protein.

D. Western Blot Analysis of Beta-amyloid Synpep Antisera Using Beta-gal-thr-Beta-amyloid (655–751) Fusion Protein Cell pellets of *E. coli* W3110 (pAPCP118-3) and W3110 (pTRP83-1) cultures induced with 3-beta-indoleacrylic acid were boiled in Laemmli gel sample buffer and electrophoresed in 12% SDS polyacrylamide. The second transformed strain is a negative control which contains all proteins except for the beta-gal-thr-beta-amyloid (655–741) fusion. The gels were then electroblotted to nitrocellulose, incubated first with APCP synpep antisera collected from immunized rabbits, and then incubated with $^{125}$I-Staphylococcus protein A to identify bound antibody (Johnson, D. A. et al., *Gene Anal Tech* (1984) 1:3). An autoradiogram was generated from these nitrocellulose filters which demonstrated crossreactivity between anti-APCP3 serum and the fusion protein, Synpep APCP3 is comprised of amino acids 705–719 of FIG. 1 which are included within the beta-amyloid portion of the fusion protein. Cross-reactivity was also observed for other beta-amyloid synpep antisera.

EXAMPLE 3

Generation of Polyclonal and Monoclonal Antibodies Against beta-amyloid-related Protein Using Live Recombinant Vaccinia Virus 1. Construction of Plasmid pFL4T4B The construction of the plasmid which allowed for the generation of polyclonal and monoclonal antibodies is schematically represented in FIG. 10. Plasmid pGEM-3 TM (Promega-Biotec) was EcoRI-digested and treated with calf intestinal phosphatase in accordance with Maniatis, et al. Fifty nanograms of the purified 1.06Kb EcoRI fragment derived from lambda APCP168i4 were mixed with 10 nanograms EcoRI digested pGEM-3 TM and incubated with T4 DNA ligase in a total volume of 20 ul for 30 min at 25° C. *E. coli* strain MC1061 was made competent for transformation by the CaCl$_2$ method and transformed with the ligation mix. Resulting ampicillin resistant colonies were grown overnight in 2 ml L-amp broth from which plasmid DNA was prepared by the Triton-lysis method (Maniatis et al.). Plasmids were screened for the correct orientation by digestion with HindIII. A plasmid having 150 and 3700 bp HindIII restriction fragments was chosen and designated p4BI. The resulting plasmid p4BI was digested with HindIII, relegated with T4 ligase for 30 minutes at 25° C. and competent MC1061 cells were transformed with the ligation mixture. Plasmids were screened for loss of the 130 bp HindIII fragment by EcoRI digestion. A plasmid containing a single EcoRI site was chosen and designated p4B DELTA RI. Ten nanograms of plasmid p4B DELTA RI was EcoRI-digested, treated with calf intestinal alkaline phosphatase, and ligated with 100 nanograms of the purified ~2 kb EcoRI fragment derived from lambda APCP168i4. The ligation mixture was used to transform competent MC1061 cells. Resulting ampicillin-resistant colonies were grown overnight in L-amp broth and plasmid DNA was prepared. Plasmids were screened for the correct orientation by digestion with BamHI and HindIII. A plasmid having a 1.5 kb BamHI and an ~1.5 kb BamHI-HindIII fragment was chosen and designated p4T4B. Plasmid p4T4B was digested with SmaI and XmnI and the resulting ~2.7kb fragment was eluted from 0.8% agarose followed by ethanol precipitation, dried in vacuo and resuspended in dH$_2$O.

Five ug of the vaccinia virus expression vector pSC11 (Chakrabarti et al. (1985) *Mol Cell Biol* 5:3403–3409) were digested to completion with SmaI followed by treatment with calf intestinal phosphatase. Five hundred nanograms of the purified ~2.7 kb SmaI-XmnI fragment derived from p4T4B were mixed with fifty nanograms of SmaI digested pSC11 and incubated with T4 DNA ligase in a total volume of 20 ul for 16 hours at 15° C overnight. *E. coli* strain MC1061 was transformed with the ligation mix. Resulting ampicillin resistant colonies were grown overnight and plasmid DNA was isolated by the rapid boiling method (Maniatis et al.). Plasmids were screened for insertion and correct orientation by digestion with EcoR1. A plasmid having both an ~2500 bp and an ~600 bp EcoR1 fragment was chosen and designated pFL4T4BV.

Monoclonal and polyclonal antibodies against full length beta-amyloid-related protein is generated by using a novel method described by Yilma, T., et al. (*Hybridoma* (1987) 6:329–337). Briefly, the method enables the production of antibodies to a specified protein without the need for a purified antigen (protein) in either the immunization or screening phase of the procedure. The methods make use of the vaccinia virus cloning vectors (Smith et al., *Nature* (1983) 302:490–495) which can be genetically engineered to carry isolated genes. The infectious recombinant vaccinia virus may then be used to immunize mice. Two weeks after infection, mice are sacrificed and their spleen cells are fused with myeloma cells for monoclonal antibody production as described in the classical approach developed by Kohler and Milstein (1973) *Nature* 256:495. Alternatively, rabbits can be conventionally immunized with the infectious vaccinia virus recombinant to generate polyclonal antisera.

Ten ug of plasmid p4T4BV is used to transfect CV-1 monkey kidney cells infected with wild-type vaccinia virus according to standard methods (Mackett et al., *J Virol* (1984) 49:857–864). TK$^-$ recombinants are isolated by plaque assay on TK$^-$ cells in the presence of 25 ug/ml Bromodeoxyuridine (BUdR). For plaque assays involving blue color production, as in the case of the pSC11 vaccinia virus coexpression vector, 300 ug of X-Gal per milliliter is placed in the agarose overlay, and plaques visualized after 4-6 hrs at 37° C. Plaques are purified two to three times in succession. DNA from the recombinant virus is examined by restriction endonuclease analysis and DNA hybridization to $^{32}$P-nick-translated 2091 bp EcoRI fragment from lambda APCP1-68i4 to confirm the predicted structure.

Recombinant virus carrying the complete beta-amyloid-related cDNA sequence of lambda APCP168i4 is isolated and amplified to high titer ($1 \times 10^{8-9}$ PFU/ml). These recombinant viruses are used to immunize rabbits and mice for the subsequent production of polyclonal and monoclonal antibodies respectively, against full length beta-amyloid-related protein(s) using well established methods. The various antisera are screened either for their ability to specifically immunoprecipitate the correct size protein from $^{35}$S-methionine-labeled CV-1 cells which have been infected with an beta-amyloid-related protein virus recombinant or for their ability to detect denatured protein on a western blot of similar cells which have not been exposed to radiolabeled amino acid.

EXAMPLE 4

Expression of Beta-amyloid-Related Protein (1-751) in Cultured Mammalian Cells

To facilitate the expression of beta-amyloid-related protein in mammalian cells, a plasmid is constructed such that the coding segment for the protein is fused to a powerful regulated promoter derived from the human metallothionein II (hMTII) gene. This procedure is pMTSV40 polyA Bam was derived from phGH-SV(10) vector by digestion of phGH-SV(10) with BamHI and SmaI restriction enzymes, followed by incubation with DNA polymerase I (Klenow fragment) in order to create blunt-ended molecules. The blunt ends are subsequently ligated to BamHI linkers, cut with BamHI, and relegated to allow for recircularization. This step removes all of the human growth hormone genomic sequence from phGH-SV(10) except for most of the 3' untranslated region of the mRNA and genomic sequences encoding putative 3' transcriptional stop and processing signals. For the mammalian cell expression construct, pMTSV40 polyA Bam is BamHI-digested, then incubated with all four nucleoside triphosphates and with DNA polymerase I to create blunt ends. This fragment is subsequently ligated with the purified 2678 bp SmaI-XmnI fragment derived from p4T4B (described previously). The recombinant molecules are introduced into MC1061 by transformation.

Chinese hamster ovary (CHO)-K1 cells are grown in a medium composed of a 1:1 mixture of F12 medium and DME medium with 10% fetal calf serum. The competent cells are co-transformed with the recombinant expression vector and pSU2:NEO (Southern, P., et al., (1982) *J Mol Appl Genet* 1:327-341). pSV2:NEO contains a functional gene conferring resistance to the neomycin analog G418. In the transformation, 500 ng of pSV2:NEO and 5 ug of the recombinant vector are applied to a 60 mm dish of CHO cells as a calcium phosphate-DNA co-precipitate as described by Graham, F. L. and Van der Eb, A. J. (1973) Virology 52:456-467. Growth of the cells in the antibiotic G418 as described by Southern et al. will yield a pool of stably transfected CHO cells containing expression vector DNA with the capacity to express beta-amyloid-related mRNA and protein.

EXAMPLE 5

Figure 12:
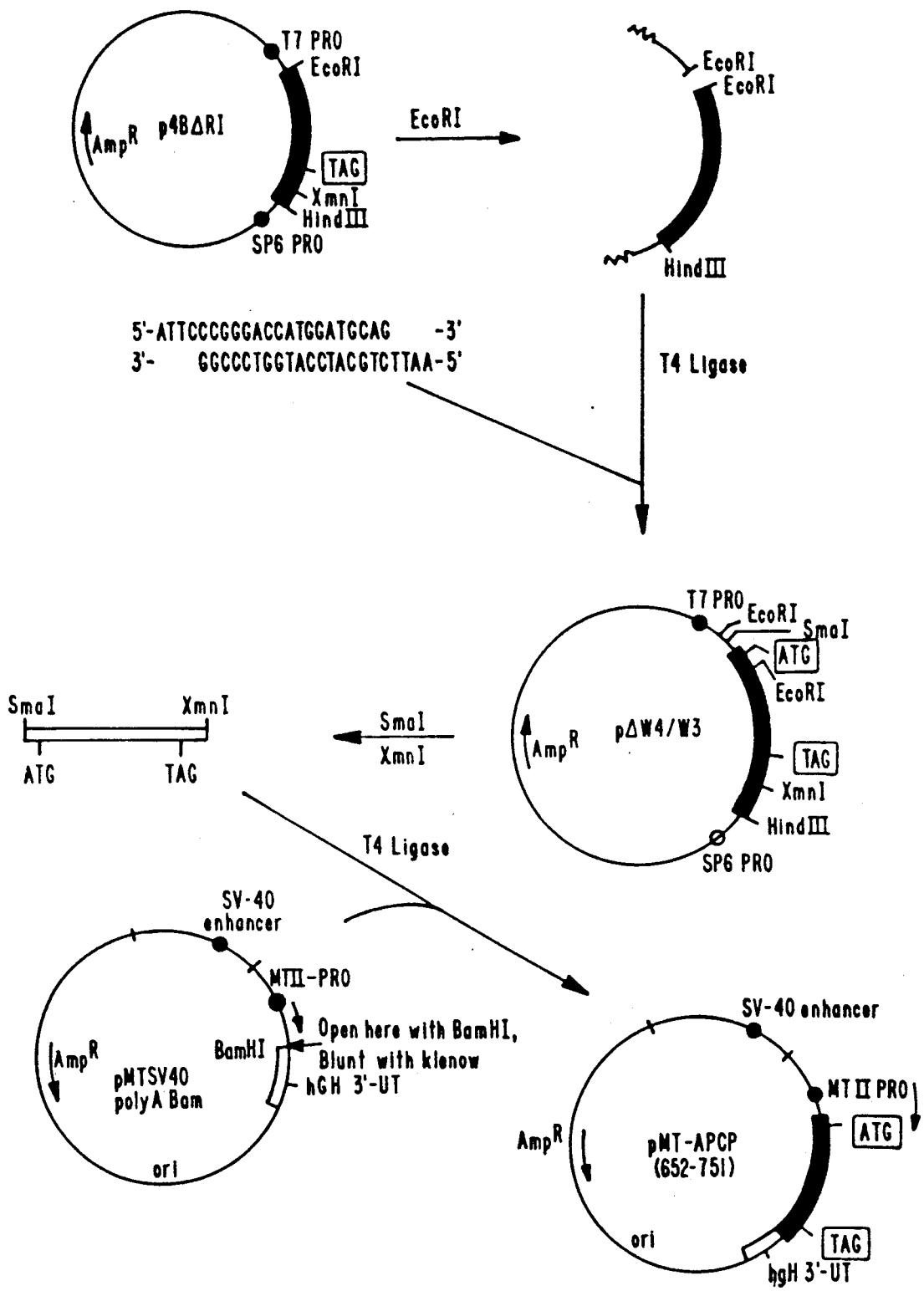
FIG. 12 shows the construction of an expression vector for the production of the beta-amyloid-related protein described in FIG. 5, when the methionine encoded immediately upstream from the beta-amyloid core protein sequence is used as an initiating methionine.

Expression of Beta-amyloid-related Protein (652-751) in Cultured Mammalian Cells A mammalian cell expression vector encoding for the production of a beta-amyloid-related protein can be constructed as shown in FIG. 12 as follows: the p4B DELTA RI vector of FIG. 10 is linearized by digestion with EcoRI. The vector is mixed with two oligonucleotides having the sequences:

```
5'-ATTCCCGGGACCATGGATGCAG-3'
3'-GGCCCTGGTACCTACGTCTTAA-5'
``` and ligated using T4 DNA ligase. These oligonucleotides reconstruct the Met-Asp-Ala codons of lambda SM2W4 and precede them by EcoRI and SmaI sites and follow them with another EcoRI site.

Competent *E. coli* strain DH1 cells are transformed with the mixture and ampicillin-resistant bacteria are selected by growth on L-Amp plates. A transformant containing the oligonucleotide pair inserted into the EcoRI site in the proper orientation is selected by standard screening techniques and designated DELTA W4/W3. Plasmid DNA DELTA W4/W3 is digested with SmaI and XmnI to remove sequences encoding the beta-amyloid-related protein described in FIG. 5 and the correct piece is isolated by gel purification.

This piece can then be inserted into the mammalian cell expression vector pMTSV40 polyA Bam which has been linearized with BamHI and rendered blunt-ended as described above in Example 4. The resulting vector, pMT-APCP (652-751) can be used for the production of the beta-amyloid-related protein (652-751).

EXAMPLE 6

Assay to Distinguish Genetic Variants of Beta-amyloid-Related Protein mRNA Species The ability to distinguish between genetic variants of beta-amyloid-related protein mRNA species using oligonucleotide probes is demonstrated herein.

A diagnostic assay for Alzheimer's disease might take the form of distinguishing between two closely related genetic variants of beta-amyloid-related proteins or their mRNAs, and quantitating the relative levels of expression of these proteins or mRNAs. FIG. 8 provides an example of the use of the invention sequences to provide a standard for the diagnostic assay.

Total cellular RNA or cytoplasmic RNA was prepared from human cells in culture or human brain tissue (Alzheimer's brain or normal brain) with or without removal of nuclei (cytoplasmic or total, respectively) by the guanidine thiocyanate/CsCl method as described by Maniatis et al. The samples corresponding to the numbering in FIG. 8 are: (1) total RNA from IMR-32 cells (ATCC #CCL127), a mixed neuroblastoma and fibroblast culture; (2) total RNA from MRC5 cells (ATCC #CCL171), a normal fibroblast; (3) total RNA from HeLa cells (ATCC #CCL2.2), an epitheloid cell; (4) cytoplasmic RNA from MRC5 cells; (5) cytoplasmic RNA from HeLa cells; (6) total RNA from HL-60 cells (ATCC #CCL240), a promyelocytic leukemia; (7) total RNA from HL-60 cells which have been treated with 12-tetra-decanoyl-phorbol-13-acetate to induce differentiation of the cells to macrophages; (8) total RNA from normal cerebellum samples; (9) total RNA from normal frontal cortex samples; (10) total RNA from an Alzheimer's individual's frontal cortex; and (11) total RNA from a normal parietal cortex. RNA was fractionated by oligo-dT cellulose chromatography, electrophoresed on a formaldehyde agarose gel, and blot-transferred to nitrocellulose (all as described in Maniatis et al.). Filters were baked, prehybridized and hybridized to the indicated probes according to standard protocols.

The probes indicated are: (1) Junction, a 30 base oligonucleotide #2733, specific for the Kang et al. sequence, as described above in the detailed description of the invention; (2) Insert, a 60 base oligonucleotide #2734 specific for the beta-amyloid-related sequences described in FIG. 1, and as described above; and (3) an 1800 bp human actin cDNA insert, isolated from the plasmid pHFBA-1 (Ponte, P., et al. (1984) *Nuc Acids Res* 12:1687-1696. Oligonucleotide probes were end-labeled with [$^{32}$P]-dCTP by incubation with terminal transferase according to manufacturer's suggestions. Actin insert was radiolabeled with [32P]-CTP by nick-translation. After hybridization, the filters hybridized to oligonucleotides were washed at 1×S.S.C., 55° C. The filter hybridized to actin was washed at 0.1×SSC at 55° C. Filters were then exposed to X-ray film to produce the autoradiogram shown. The insert probe detects the beta-amyloid related protein mRNA described in FIG. 1 in all samples examined. The junction probe detects the beta-amyloid-related mRNA described by Kang et al. in all cells except HeLa and MRC5. The actin probe is a control which is expected to hybridize to an abundant RNA in all cells.

EXAMPLE 7

Bacterial Expression of Beta-amyloid-Related Protein (289-345)

A. Construction of Plasmid pAPCP125-2

A synthetic gene was assembled according to the teaching of Example 2 for beta-amyloid-related protein (289-345) from three pairs of oligodeoxyribonucleotides (illustrated in FIG. 9D) utilizing *E. coli* preferred codon choice for highly expressed genes, and a hydroxylamine cleavage site (Asn-Gly) was inserted preceding amino acid 289 (Glu) to permit release of the polypeptide from a fusion protein. The expression vector pTRP83-1 was digested with restriction endonucleases EcoRI and HindIII and the linearized plasmid purified from a 0.6% agarose gel. Fifty ug of plasmid DNA and 200 ug of synthetic gene DNA were ligated using T4 DNA ligase and *E. coli* MC1061 was transformed with the ligation. Ampicillin-resistant colonies were grown overnight in L broth containing 100 ug/ml ampicillin and alkaline plasmid preps were made. The resulting plasmid DNA was digested with BamHI restriction endonuclease to confirm insertion of the gene within the vector by release of an approximately 350 bp fragment. One plasmid receiving the synthetic gene insert was designated pAPCP125-2.

B. Expression of Beta-amyloid-Related Fusion Polypeptide (289-345)

The plasmid pAPCP125-2 is designed to express a 74 amino acid beta-galactosidase-threonine-beta-amyloid-related fusion protein under the control of the *E. coli* tryptophan promoter/operator. *E. coli* strain W3110 is transformed with plasmid pAPCP125-2 and one of the resulting ampicillin resistant colonies is grown as described in Example 2. Expression is induced by the addition of 3-beta-indoleacrylic acid at a final concentration of 25 ug/ml. After 5 hrs induction, a 1 ml aliquot of cells is withdrawn from the culture, harvested by centrifugation, then boiled in 100 ul of Laemmli protein sample buffer for electrophoresis through a 16% SDS-polyacrylamide gel by standard methodologies. Assessment of inclusion body formation is made by phase contrast microscopy (1000×). Expression levels are estimated by Coomassie blue staining of the gel followed by densitometer scan to quantitate the intensity of protein bands. Cells to be used for protein purification are harvested by centrifugation, washed with 10 mM Tris-HCl, pH 7.5, and the cell pellet frozen at −20° needed.

C. Purification of Beta-gal-thr-Beta-amyloid-related Protein (289-345)

The fusion protein is purified as described for the beta-gal-thr-beta-amyloid-related (655-751) fusion protein (Example 2) in the absence of PMSF and aprotinin. A series of washes from 2M urea to 4M urea removes other proteins and further enriches fusion protein found in inclusion bodies. If further purification is desired, the fusion protein is solubilized in 6-8M urea, and a gel filtration or ion exchange chromatography step is included. If not, the fusion protein is solubilized in 6M guanidium hydrochloride with hydroxylamine under the conditions described by Moks et al., *Biochem* (1987) 26:5239-5244 for cleavage between the Asn and Gly residues releasing beta-amyloid-related protein (289-345) with a Gly residue at its amino-terminus. The cleaved peptides are purified by reversed phase high pressure liquid chromatography, ion exchange or gel filtration chromatography. The purified beta-amyloid-related protein is then reduced and reoxidized by methods described by Tan and Kaiser, *J Org Chem* (1976) 41:2787 and *Biochemistry* (1977) 16:1531-1541, to reform disulfide bonds between the six Cys residues. Successful reoxidation of bovine pancreatic trypsin inhibitor (aprotinin) also containing six Cys residues and produced in *E. coli* has been accomplished by these methods (von Wilcken-Bergmann et al., *EMBO Journal* (1986) 5:3219-3225.

While preferred embodiments of making and using the invention have been described, it will be appreciated that various changes and modifications can be made without departing from the invention.

The following cultures have been deposited with the American Type Culture Collection (ATCC), Rockville, Md., USA for patent purposes. Bacteriophage phages lambda SM2, lambda SM2W9, and lambda APCP168i4 were deposited under the conditions specified by the Budapest Treaty on the International Recognition of the Deposit of Microorganisms (Budapest Treaty).

| Culture | Accession No. | Deposit Date |
|---|---|---|
| lambda SM2 | 40279 | 13 November 1986 |
| SM2W4 | 40299 | 29 December 1986 |
| SM2W3 | 40300 | 29 December 1986 |
| lambda SM2W9 | 40304 | 29 January 1987 |
| lambda APCP168i4 | 40347 | 1 July 1987 |

Availability of the deposited strains are not to be construed as a license to practice the invention in contravention of the rights granted under the authority of any government in accordance with its patent laws.

We claim:

1. An isolated native, cloned recombinant or synthetic DNA sequence useful in the prognosis and diagnosis of Alzheimer's disease in human subjects comprising the DNA sequence of FIG. 1.

2. A subfragment of the DNA sequence of claim 1 wherein the subfragment corresponds to the 168 basepair insert fragment of the beta-amyloid-related gene product of bacteriophage lambda ACPC168i4.

3. An isolated native, cloned recombinant or synthetic DNA sequence corresponding to nucleotides 864 to 1035 in FIG. 1.

4. The DNA of claim 3 which encodes the amino acid sequence:

GluValCysSerGluGlnAlaGluThrGlyProCysArgAlaMet
IleSerArgTrpTyrPheAspValThrGluGlyLysCysAla
ProPhePheTyrGlyGlyCysGlyGlyAsnArgAsnAsnPhe
AspThrGluGluTyrCysMetAlaValCysGlySerAlaIle.

5. A reagent for use in the diagnosis of Alzheimer's disease in a human patient comprising the DNA sequence of claim 2.

* * * * *